US012454551B2

(12) United States Patent
Nakchbandi et al.

(10) Patent No.: US 12,454,551 B2
(45) Date of Patent: Oct. 28, 2025

(54) PEPTIDES AS INHIBITORS OF FIBROTIC MATRIX ACCUMULATION

(71) Applicant: Max-Planck-Gesellschaft zur Förderung der Wissenschaften e.V., Munich (DE)

(72) Inventors: Inaam Nakchbandi, Hirschberg (DE); Stefan Hamelmann, Heidelberg (DE); Stephan Uebel, Wofratshausen (DE)

(73) Assignee: Max-Planck-Gesellschaft zur Forderung der Wissenschaften e.V., Munich (DE)

( * ) Notice: Subject to any disclaimer, the term of this patent is extended or adjusted under 35 U.S.C. 154(b) by 848 days.

(21) Appl. No.: 17/631,533

(22) PCT Filed: Jul. 28, 2020

(86) PCT No.: PCT/EP2020/071319

§ 371 (c)(1),
(2) Date: Jan. 31, 2022

(87) PCT Pub. No.: WO2021/018923

PCT Pub. Date: Feb. 4, 2021

(65) Prior Publication Data

US 2022/0267378 A1 Aug. 25, 2022

(30) Foreign Application Priority Data

Jul. 31, 2019 (EP) .................................... 19189468
Aug. 30, 2019 (EP) .................................... 19194798

(51) Int. Cl.

| | |
|---|---|
| ***A61K 38/00*** | (2006.01) |
| ***A61P 1/16*** | (2006.01) |
| ***A61P 11/00*** | (2006.01) |
| ***A61P 35/00*** | (2006.01) |
| ***C07K 7/06*** | (2006.01) |
| ***C07K 7/52*** | (2006.01) |
| ***C07K 7/64*** | (2006.01) |

(52) U.S. Cl.
CPC .................. *C07K 7/52* (2013.01); *A61P 1/16* (2018.01); *A61P 11/00* (2018.01); *A61P 35/00* (2018.01); *A61K 38/00* (2013.01)

(58) Field of Classification Search
CPC .. A61K 38/00; A61P 1/16; A61P 11/00; A61P 35/00; C07K 7/06; C07K 7/52
See application file for complete search history.

(56) References Cited

U.S. PATENT DOCUMENTS 8,288,341 B2 * 10/2012 Benner ..................... A61P 1/00 514/21.7
8,470,976 B2 * 6/2013 Chook .................. C07K 14/47 530/358
9,382,310 B2 * 7/2016 Mirochnitchenko .. C07K 14/33
11,371,070 B2 * 6/2022 Li ........................... A23L 33/18

OTHER PUBLICATIONS

International Search Report and Written Opinion for International Patent Application No. PCT/EP2020/071319 dated Nov. 12, 2020, 18 pages.

* cited by examiner

*Primary Examiner* — Julie Ha
(74) *Attorney, Agent, or Firm* — Amin, Turocy & Watson, LLP

(57) ABSTRACT

Peptides that inhibit overproduction and/or excess accumulation of extracellular matrix in an organ or tissue are described. The inventive peptides have the general sequence Xa-Leu-Gln-Gly-Xb (SEQ ID NO: 1), wherein Xa is selected from Pro-Gly, Gly and Ac-Gly and Xb is selected from Glu and Glu-NH2, and are able of inhibit overproduction and excess accumulation of extracellular matrix in an organ or tissue both as linear peptides and as cyclic peptides. In particular the peptides disclosed herein can be used for treating fibrotic conditions characterized by an excess accumulation of extracellular matrix such as liver fibrosis, cirrhosis of the liver, lung fibrosis, chronic respiratory failure, cardiac fibrosis, ischemic heart disease, heart failure, diabetic nephropathy, glomerulonephritis, myelofibrosis, and various types of cancers.

18 Claims, 4 Drawing Sheets

Specification includes a Sequence Listing.

SEQUENCE LISTING

```
<160> NUMBER OF SEQ ID NOS: 16

<210> SEQ ID NO 1
<211> LENGTH: 5
<212> TYPE: PRT
<213> ORGANISM: Homo sapiens
<220> FEATURE:
<221> NAME/KEY: NON_STD
<222> LOCATION: 1
<223> OTHER INFORMATION: Xaa at position 1 is Pro-Gly, Gly, or Ac-Gly
<220> FEATURE:
<223> OTHER INFORMATION: Artificial
<220> FEATURE:
<221> NAME/KEY: NON_STD
<222> LOCATION: 5
<223> OTHER INFORMATION: Xaa at position 5 is Glu or Glu-NH2

<400> SEQUENCE: 1

Xaa Leu Gln Gly Xaa
1               5


<210> SEQ ID NO 2
<211> LENGTH: 5
<212> TYPE: PRT
<213> ORGANISM: Homo sapiens
<220> FEATURE:
<223> OTHER INFORMATION: Artificial

<400> SEQUENCE: 2

Gly Leu Gln Gly Glu
1               5


<210> SEQ ID NO 3
<211> LENGTH: 5
<212> TYPE: PRT
<213> ORGANISM: Homo sapiens
<220> FEATURE:
```

-continued

<221> NAME/KEY: MOD_RES
<222> LOCATION: 1
<223> OTHER INFORMATION: N-terminal acetylation
ACETYLATION
<220> FEATURE:
<223> OTHER INFORMATION: Artificial

<400> SEQUENCE: 3

Gly Leu Gln Gly Glu
1 5

<210> SEQ ID NO 4
<211> LENGTH: 5
<212> TYPE: PRT
<213> ORGANISM: Homo sapiens
<220> FEATURE:
<223> OTHER INFORMATION: Artificial
<220> FEATURE:
<221> NAME/KEY: MOD_RES
<222> LOCATION: 5
<223> OTHER INFORMATION: AMIDATION
C-terminal amidation

<400> SEQUENCE: 4

Gly Leu Gln Gly Glu
1 5

<210> SEQ ID NO 5
<211> LENGTH: 5
<212> TYPE: PRT
<213> ORGANISM: Homo sapiens
<220> FEATURE:
<221> NAME/KEY: SITE
<222> LOCATION: 1..5
<223> OTHER INFORMATION: peptide bond between the amino-terminus and the
carboxyl-terminus
<220> FEATURE:
<223> OTHER INFORMATION: Artificial

<400> SEQUENCE: 5

Gly Leu Gln Gly Glu
1 5

<210> SEQ ID NO 6
<211> LENGTH: 6
<212> TYPE: PRT
<213> ORGANISM: Homo sapiens
<220> FEATURE:
<221> NAME/KEY: SITE
<222> LOCATION: 1..6
<223> OTHER INFORMATION: peptide bond between the amino-terminus and the
carboxyl-terminus
<220> FEATURE:
<223> OTHER INFORMATION: Artificial

<400> SEQUENCE: 6

Pro Gly Leu Gln Gly Glu
1 5

<210> SEQ ID NO 7
<211> LENGTH: 5
<212> TYPE: PRT
<213> ORGANISM: Homo sapiens
<220> FEATURE:
<223> OTHER INFORMATION: Artificial

<400> SEQUENCE: 7

Gly Leu Asn Gly Glu
1 5

<210> SEQ ID NO 8
<211> LENGTH: 5
<212> TYPE: PRT
<213> ORGANISM: Homo sapiens
<220> FEATURE:
<221> NAME/KEY: MOD_RES
<222> LOCATION: 1
<223> OTHER INFORMATION: ACETYLATION
N-Terminal Acetylation
<220> FEATURE:
<223> OTHER INFORMATION: Artificial

<400> SEQUENCE: 8

Gly Leu Asn Gly Glu
1 5

<210> SEQ ID NO 9
<211> LENGTH: 5
<212> TYPE: PRT
<213> ORGANISM: Homo sapiens
<220> FEATURE:
<223> OTHER INFORMATION: Artificial
<220> FEATURE:
<221> NAME/KEY: MOD_RES
<222> LOCATION: 5
<223> OTHER INFORMATION: C-terminal amidation
AMIDATION

<400> SEQUENCE: 9

Gly Leu Asn Gly Glu
1 5

<210> SEQ ID NO 10
<211> LENGTH: 5
<212> TYPE: PRT
<213> ORGANISM: Homo sapiens
<220> FEATURE:
<221> NAME/KEY: SITE
<222> LOCATION: 1..5
<223> OTHER INFORMATION: peptide bond between the amino-terminus and the
carboxyl-terminus
<220> FEATURE:
<223> OTHER INFORMATION: Artificial

<400> SEQUENCE: 10

Gly Leu Asn Gly Glu
1 5

<210> SEQ ID NO 11
<211> LENGTH: 6
<212> TYPE: PRT
<213> ORGANISM: Homo sapiens
<220> FEATURE:
<221> NAME/KEY: SITE
<222> LOCATION: 1..6
<223> OTHER INFORMATION: peptide bond between the amino-terminus and the
carboxyl-terminus
<220> FEATURE:
<223> OTHER INFORMATION: Artificial

<400> SEQUENCE: 11

Pro Gly Leu Asn Gly Glu
1 5

<210> SEQ ID NO 12
<211> LENGTH: 5
<212> TYPE: PRT
<213> ORGANISM: Homo sapiens
<220> FEATURE:
<221> NAME/KEY: NON_STD -continued

```
<222> LOCATION: 3
<223> OTHER INFORMATION: Xaa at position 3 is Hydroxyproline

<400> SEQUENCE: 12

Gly Leu Xaa Gly Glu
1               5


<210> SEQ ID NO 13
<211> LENGTH: 5
<212> TYPE: PRT
<213> ORGANISM: Homo sapiens
<220> FEATURE:
<221> NAME/KEY: MOD_RES
<222> LOCATION: 1
<223> OTHER INFORMATION: N-terminal acetylation
      ACETYLATION
<220> FEATURE:
<223> OTHER INFORMATION: Artificial
<220> FEATURE:
<221> NAME/KEY: NON_STD
<222> LOCATION: 3
<223> OTHER INFORMATION: Xaa at position 3 is Hydroxyproline

<400> SEQUENCE: 13

Gly Leu Xaa Gly Glu
1               5


<210> SEQ ID NO 14
<211> LENGTH: 5
<212> TYPE: PRT
<213> ORGANISM: Homo sapiens
<220> FEATURE:
<223> OTHER INFORMATION: Artificial
<220> FEATURE:
<221> NAME/KEY: NON_STD
<222> LOCATION: 3
<223> OTHER INFORMATION: Xaa at position 3 is Hydroxyproline
<220> FEATURE:
<221> NAME/KEY: MOD_RES
<222> LOCATION: 5
<223> OTHER INFORMATION: C-terminal amidation
      AMIDATION

<400> SEQUENCE: 14

Gly Leu Xaa Gly Glu
1               5


<210> SEQ ID NO 15
<211> LENGTH: 5
<212> TYPE: PRT
<213> ORGANISM: Homo sapiens
<220> FEATURE:
<221> NAME/KEY: SITE
<222> LOCATION: 1..5
<223> OTHER INFORMATION: peptide bond between the amino-terminus and the
      carboxyl-terminus
<220> FEATURE:
<223> OTHER INFORMATION: Artificial
<220> FEATURE:
<221> NAME/KEY: NON_STD
<222> LOCATION: 3
<223> OTHER INFORMATION: Xaa at position 3 is Hydroxyproline

<400> SEQUENCE: 15

Gly Leu Xaa Gly Glu
1               5


<210> SEQ ID NO 16
<211> LENGTH: 6
<212> TYPE: PRT
<213> ORGANISM: Homo sapiens
```

-continued

```
<220> FEATURE:
<221> NAME/KEY: SITE
<222> LOCATION: 1..6
<223> OTHER INFORMATION: peptide bond between the amino-terminus and the
      carboxyl-terminus
<220> FEATURE:
<223> OTHER INFORMATION: Artificial
<220> FEATURE:
<221> NAME/KEY: NON_STD
<222> LOCATION: 3
<223> OTHER INFORMATION: Xaa at position 4 is Hydroxyproline

<400> SEQUENCE: 16

Pro Gly Leu Xaa Gly Glu
1               5
```

PEPTIDES AS INHIBITORS OF FIBROTIC MATRIX ACCUMULATION

SPECIFICATION

The present invention relates to peptides that inhibit overproduction and/or excess accumulation of extracellular matrix in an organ or tissue. The inventive peptides have the general sequence Xa-Leu-Gln-Gly-Xb (SEQ ID NO:1), wherein Xa is selected from Pro-Gly, Gly and Ac-Gly and Xb is selected from Glu and Glu-$NH_2$, and are able of inhibit overproduction and excess accumulation of extracellular matrix in an organ or tissue both as linear peptides and as cyclic peptides. In particular the peptides disclosed herein can be used for treating fibrotic conditions characterized by an excess accumulation of extracellular matrix such as liver fibrosis, cirrhosis of the liver, lung fibrosis, chronic respiratory failure, cardiac fibrosis, ischemic heart disease, heart failure, diabetic nephropathy, glomerulonephritis, myelofibrosis, and various types of cancers such as breast cancer, uterus cancer, prostate cancer, pancreas cancer, colon cancer, skin cancer, blood cell cancers, cancers of the central nervous system, fibroids, fibroma, fibroadenomas and fibrosarcomas.

BACKGROUND OF THE INVENTION

The invention provides novel peptides which can be used to treat conditions associated with an excessive matrix accumulation in tissues or organs. The therapeutic effects of the invention result from a reduction in or prevention of the overproduction of extracellular matrix. One possibility includes but is not limited to inhibiting TGFβ (transforming growth factor-B) to effectively diminish the TGFβ induced component of extracellular matrix deposition.

Cells in organs are held together through a network of several types of extracellular matrix molecules including collagens and fibronectin, which are produced by many cell types including various subpopulations of fibroblasts. In almost all types of diseases there is a change in matrix composition or distribution. Changes in matrix composition that develop whenever a fibrotic process has been initiated directly affect the function of fibroblastic cells by stimulating matrix production. These changes also affect the responsiveness to profibrotic cytokines as well as matrix stiffness, which increases fibroblastic differentiation, further facilitating the production of matrix.

TGFβ is an important molecule involved in matrix accumulation. It is produced by a variety of cells including activated immune cells and fibroblastic cells and can enhance matrix production by stimulating the immune response and increasing activation of the fibroblasts to produce matrix. It is stored in the matrix in an inactive form that needs to be released from the matrix, a process that requires the action of cell receptors called integrins. Some TGFβ can also be released through the action of proteins such as the so called matrix metalloproteases produced by the cells without involvement of integrins. Once released, TGFβ binds to its receptor and starts a signaling cascade. There is a large variability in the action of TGFβ depending both on the concentration available and on the cell type involved. TGFβ is viewed as a key mediator of fibrosis and scar tissue, and it is also almost universally found in cancer suggesting its involvement in cancer growth and progression. TGFβ fibrogenic action results from simultaneous stimulation of matrix protein synthesis, inhibition of matrix degradation, and turnover and enhanced cell-matrix interactions through modulation of integrin receptors that facilitate assembly of extracellular matrix. In fibrotic diseases overproduction of TGFβ results in excess accumulation of extracellular matrix which leads to tissue fibrosis and eventually organ failure. Fibrotic conditions associated with excessive extracellular matrix accumulation due to TGFβ overproduction are for example liver fibrosis, cirrhosis of the liver, lung fibrosis, chronic respiratory failure, cardiac fibrosis, heart failure, ischemic heart disease, diabetic nephropathy, glomerulonephritis, myelofibrosis, and various types of cancers such as breast cancer, uterus cancer, prostate cancer, pancreas cancer, colon cancer, skin cancer, blood cell cancers, cancers of the central nervous system, fibroids, fibroma, fibroadenomas and fibrosarcomas.

Moreover, many of the main cell-cell and cell-matrix interactions that regulate fibrosis are mediated by cell adhesion receptors called integrins, and the integrin family seems to be a key regulator of chronic inflammation and fibrosis. Fibrosis models in multiple organs have demonstrated that integrins have profound effects on the fibrotic process, and that they are upregulated in different types of fibrosis, such as liver, renal and skin fibrosis. In addition to their direct effects on cellular proliferation and survival, it has been shown that integrins can activate latent TGFβ. Pre-clinical data suggest that integrin targeting could be a promising treatment of fibrotic diseases, however much less is currently known about the risks of these interventions. Recently, studies aimed at anti-fibrotic therapies have used strategies to manipulate integrins, such as antibody blockade and small molecule inhibitors.

EP 0494264 B1 is a patent providing a method for treating or arresting the progress of pathologies characterized by an accumulation of extracellular matrix components by providing an agent to suppress the activity of transforming growth factor β (TGFβ), which can be an anti-TGFβ antibody or an Arg-Gly-Asp (RGD) containing peptide of 4-50 amino acids. Pathologies which can be so treated include various fibrotic diseases, glomerulonephritis, adult respiratory distress syndrome, cirrhosis of the liver, fibrotic cancer, fibrosis of the lungs, arteriosclerosis, post myocardial infarction, cardiac fibrosis, post-angioplasty restenosis, renal interstitial fibrosis and scarring.

U.S. Pat. No. 7,713,924 B2 relates to methods and compositions for reducing and preventing the excess accumulation of extracellular matrix using a combination of agents that inhibit TGFβ, alone or in combination with agents that degrade excess accumulated extracellular matrix. Treatable conditions can be fibrotic diseases and scarring that result from excess accumulation of extracellular matrix. The inhibitor composition can comprise two or three agents: the first one or two agents can be inhibitors of aldosterone, inhibitors of angiotensin II, anti-TGFβ antibodies, inhibitors of renin, proteoglycans and ligands for the TGFβ receptor, the third agent is a PAI inhibitor.

It is the objective of the present invention to provide novel peptides and/or pharmaceutically acceptable salts thereof which can be used as pharmaceutically active agents, especially for the treatment of fibrotic conditions associated with an excess matrix accumulation, as well as compositions comprising at least one of those peptides and/or pharmaceutically acceptable salts thereof as pharmaceutically active ingredients.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The invention provides novel peptides which can be used to treat conditions associated to an excessive matrix accumulation in tissues or organs. The therapeutic effects of the invention result from a reduction in or prevention of the excess matrix production and accumulation. Moreover the peptides could be acting through TGFβ or directly by interacting with a yet not fully characterized cell surface receptor. Since the accumulation of matrix contributes to the deterioration of organ function in several diseases we propose that these novel peptides diminish matrix accumulation and hence functional deterioration.

Therefore, the present invention provides a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and the pharmaceutically acceptable salts thereof. A preferred embodiment of the invention is directed to a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and the pharmaceutically acceptable salts thereof. SEQ ID NO: 2 refers to the pentapeptide Gly-Leu-Gln-Gly-Glu (GLQGE).

Another preferred embodiment of the invention is directed to a peptide consisting of the general sequence Xa-Leu-Gln-Gly-Xb (SEQ ID NO: 1), wherein Xa is Ac-Gly and Xb is Glu and the pharmaceutically acceptable salts thereof (SEQ ID NO: 3). A more preferred embodiment of the invention is directed to a peptide Xa-Leu-Gln-Gly-Xb (SEQ ID NO: 1), wherein Xa is Gly and Xb is Glu-$NH_2$, and the pharmaceutically acceptable salts thereof (SEQ ID NO: 4). A still more preferred embodiment of the invention is directed to a peptide consisting of the general sequence Xa-Leu-Gln-Gly-Xb, wherein Xa is Gly and Xb is Glu, and Glu binds to Gly to form the cyclic peptide (SEQ ID NO: 5):

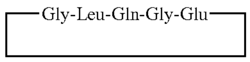

A further preferred embodiment of the invention is directed to a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

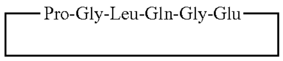

Another embodiment of the invention provides a pharmaceutical composition comprising the peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof, together with at least one pharmaceutically acceptable vehicle, excipient and/or diluent. A further embodiment of the invention provides a pharmaceutical composition comprising the peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, together with at least one pharmaceutically acceptable vehicle, excipient and/or diluent. A preferred embodiment of the invention provides a pharmaceutical composition comprising the peptide consisting of the general sequence Xa-Leu-Gln-Gly-Xb, wherein Xa is Ac-Gly and Xb is Glu (SEQ ID NO: 3), and/or the pharmaceutically acceptable salts thereof, together with at least one pharmaceutically acceptable vehicle, excipient and/or diluent. Another preferred embodiment of the invention provides a pharmaceutical composition comprising the peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, together with at least one pharmaceutically acceptable vehicle, excipient and/or diluent. Another preferred embodiment of the invention provides a pharmaceutical composition comprising the peptide consisting of the general sequence Xa-Leu-Gln-Gly-Xb, wherein Xa is Gly and Xb is Glu, and Glu binds to Gly to form the cyclic peptide (SEQ ID NO: 5):

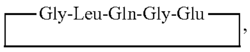, and/or the pharmaceutically acceptable salts thereof, together with at least one pharmaceutically acceptable vehicle, excipient and/or diluent.

Another preferred embodiment of the invention provides a pharmaceutical composition comprising the peptide consisting of the general sequence Xa-Leu-Gln-Gly-Xb, wherein Xa is Pro-Gly and Xb is Glu, and Pro binds to Glu to form the cyclic peptide (SEQ ID NO: 6):

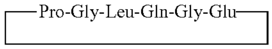

and/or the pharmaceutically acceptable salts thereof, together with at least one pharmaceutically acceptable vehicle, excipient and/or diluent.

In another aspect, the present invention provides a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof for use in the treatment of a fibrotic condition characterized by an excess accumulation of extracellular matrix in a tissue and/or an organ. In a particular aspect, the present invention provides a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, for use in the treatment of a fibrotic condition characterized by an excess accumulation of extracellular matrix in a tissue and/or an organ. In a preferred aspect, the present invention provides a peptide consisting of the general sequence Xa-Leu-Gln-Gly-Xb, wherein Xa is Ac-Gly and Xb is Glu (SEQ ID NO: 3), or Xa is Gly and Xb is Glu-$NH_2$ (SEQ ID NO: 4) and/or the pharmaceutically acceptable salts thereof, for use in the treatment of a fibrotic condition characterized by an excess accumulation of extracellular matrix in a tissue and/or an organ. In a preferred aspect, the present invention provides a peptide consisting of the general sequence Xa-Leu-Gln-Gly-Xb, wherein Xa is Gly and Xb is Glu, and Glu binds to Gly to form the cyclic peptide (SEQ ID NO: 5):

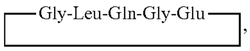, and/or the pharmaceutically acceptable salts thereof for use in the treatment of a fibrotic condition characterized by an excess accumulation of extracellular matrix in a tissue and/or an organ. In a more preferred aspect, the present invention provides a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

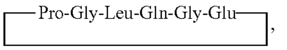, and/or the pharmaceutically acceptable salts thereof, for use in the treatment of a fibrotic condition characterized by an excess accumulation of extracellular matrix in a tissue and/or an organ.

It is preferred that said fibrotic condition is selected from the group consisting of liver fibrosis, cirrhosis of the liver, lung fibrosis, chronic respiratory failure, cardiac fibrosis, ischemic heart disease, heart failure, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

DETAILED DESCRIPTION OF THE INVENTION

The inventors have identified a sequence of five amino acids Gly-Leu-Gln-Gly-Glu or in the one-letter code GLQGE that is able to diminish matrix accumulation in a chemically induced model of liver fibrosis in mice in both cyclic and linear form, and showing a surprisingly stronger effect in comparison to similar sequences known in the prior art. In particular, the inventors have found that both the N-terminal acetylated form Ac-Gly-Leu-Gln-Gly-Glu (SEQ ID NO: 3) and the C-terminal amidated form Gly-Leu-Gln-Gly-Glu-$NH_2$ (SEQ ID NO: 4) are able to reduce matrix accumulation in a chemically induced model of liver fibrosis in mice (FIGS. 1 and 2), showing a better effect in comparison to the control peptides Ac-Gly-Leu-Asn-Gly-Glu (SEQ ID NO: 8), Gly-Leu-Asn-Gly-Glu-$NH_2$ (SEQ ID NO: 9), Ac-Gly-Leu-Hyp-Gly-Glu (SEQ ID NO: 13), Gly-Leu-Hyp-Gly-Glu-$NH_2$ (SEQ ID NO: 14). The sequences Gly-Leu-Asn-Gly-Glu (SEQ ID NO: 7) and Gly-Leu-Hyp-Gly-Glu (SEQ ID NO: 12) are known to be part of sequences that bind the collagen-binding integrins.

Moreover, the cyclic Gly-Leu-Gln-Gly-Glu (SEQ ID NO: 5) showed a stronger effect compared to the linear forms of peptide of same sequence, i.e. with N-terminal acetylation or C-terminal amidation, and also compared to the cyclic Gly-Leu-Asn-Gly-Glu (SEQ ID NO: 10) and cyclic Gly-Leu-Hyp-Gly-Glu (SEQ ID NO: 15). To notice, also the cyclic form with proline Pro-Gly-Leu-Gln-Gly-Glu (SEQ ID NO: 6) was able to significantly reduce collagen accumulation with a stronger efficacy compared to Pro-Gly-Leu-Asn-Gly-Glu (SEQ ID NO: 11) and to Pro-Gly-Leu-Hyp-Gly-Glu (SEQ ID NO: 16), but weaker compared to the cyclic Gly-Leu-Gln-Gly-Glu. (SEQ ID NO: 5). Since the accumulation of matrix contributes to the deterioration of organ function in several diseases, these peptides could be used to treat fibrotic conditions associated with excessive matrix accumulation. The underlying mechanism could be due to a direct effect of the peptide on a yet not fully characterized cell surface receptor or indirectly by affecting the amount of or the response to TGFβ, which represents a major molecule involved in the progression of several diseases. It could also be due to a direct effect on one or more cell types to diminish the production of extracellular matrix proteins.

Therefore, the present invention provides a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and the pharmaceutically acceptable salts thereof. A preferred embodiment of the invention is directed to a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and the pharmaceutically acceptable salts thereof. Another preferred embodiment of the invention is directed to a peptide consisting of the general sequence Xa-Leu-Gln-Gly-Xb, wherein Xa is Ac-Gly and Xb is Glu (SEQ ID NO: 3), and the pharmaceutically acceptable salts thereof. A more preferred embodiment of the invention is directed to a peptide Xa-Leu-Gln-Gly-Xb, wherein Xa is Gly and Xb is Glu-$NH_2$ (SEQ ID NO: 4), and the pharmaceutically acceptable salts thereof. A still more preferred embodiment of the invention is directed to a peptide consisting of the general sequence Xa-Leu-Gln-Gly-Xb, wherein Xa is Gly and Xb is Glu, and Glu binds to Gly to form the cyclic peptide (SEQ ID NO: 5):

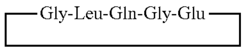

A further preferred embodiment of the invention is directed to a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

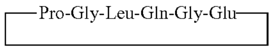

The term "peptide" refers to a compound made up of a single chain of D- or L-amino acids or a mixture of D- and L-amino acids joined by peptide bonds. Generally, peptides of the present invention are most preferably 5-6 amino acids in length.

The term "cyclic peptide" as used herein refers to a peptide Gly-Leu-Gln-Gly-Glu (SEQ ID NO: 5) and to the controls Gly-Leu-Asn-Gly-Glu (SEQ ID NO: 10), Gly-Leu-Hyp-Gly-Glu (SEQ ID NO: 15), in which the amino-terminus of the peptide is joined by a peptide bond to the carboxyl-terminus of the peptide or a side-chain of the amino acid Glu having a free carboxyl group. Preferably, the amino-terminus of Gly in the peptide Gly-Leu-Gln-Gly-Glu (SEQ ID NO: 5) is bound via a peptide bond to the carboxyl-terminus of Glu and not to the side chain carboxyl group of Glu. Also described herein are the cyclic peptides Pro-Gly-Leu-Gln-Gly-Glu (SEQ ID NO: 6), and the controls Pro-Gly-Leu-Asn-Gly-Glu (SEQ ID NO: 11) and Pro-Gly-Leu-Hyp-Gly-Glu (SEQ ID NO: 16), in which the amino-terminus of the peptide is joined by a peptide bond to the carboxyl-terminus of the peptide or a side-chain of the amino acid Glu having a free carboxyl group. Preferably, the amino-terminus of Pro in the peptide Pro-Gly-Leu-Gln-Gly-Glu (SEQ ID NO: 6) is bound via a peptide bond to the carboxyl-terminus of Glu and not to the side chain carboxyl group of Glu.

In the formulas representing selected specific peptide embodiments of the present invention, the amino- and carboxy-terminal groups, although often not specifically shown, will be understood to be in the form they would assume at physiological pH values, unless otherwise specified. Thus, the N-terminal $H^+$ and C-terminal $O^-$ (i.e. the betaine form) at physiological pH are understood to be present though not necessarily specified and shown, either in specific examples or in generic formulas. In the peptide notation used herein, the left-hand end of the molecule is the amino terminal end and the right-hand end is the carboxy-terminal end, in accordance with standard usage and convention. Of course, the basic and acid addition salts including those which are formed at non-physiological pH values are also included in the compounds of the invention.

The term "amino acid" as used herein includes the standard twenty genetically-encoded amino acids and their corresponding stereoisomers in the "D" form (as compared to the natural "L" form), omega-amino acids other naturally-occurring amino acids, unconventional amino acids (e.g. $\alpha,\alpha$-disubstituted amino acids, N-alkyl amino acids, etc.) and chemically derivatized amino acids. When an amino acid is being specifically enumerated, such as "glutamine" or "Gln" or "Q" the term refers to both L-glutamine and D-glutamine unless explicitly stated otherwise. However, the naturally occurring L-form is most preferred. Therefore, the L-form of the peptides disclosed herein and especially the L-form of Gly-Leu-Gln-Gly-Glu (SEQ ID NO: 2) are preferred. Other unconventional amino acids may also be suitable components for polypeptides of the present invention, as long as the desired functional property is retained by the polypeptide. For the peptides shown, each encoded amino acid residue, where appropriate, is represented by a three letter designation, corresponding to the trivial name of the conventional amino acid. In the present invention, in the peptide of sequence Gly-Leu-Hyp-Gly-Glu (GLOGE; SEQ ID NO: 12) the common non-proteinogenic amino acid hydroxyproline is abbreviated with Hyp when using the three letter code, and "O" when using the one letter code.

A peptide according to this invention can be synthesized by several methods, including chemical synthesis. Solid phase synthesis methods consist of the sequential addition of one or more amino acid residues or suitably protected amino acid residues to a growing peptide chain. Either the amino or carboxyl group of the first amino acid residue is protected by a suitable selectively removable protecting group. A different, selectively removable protecting group is utilized for amino acids containing a reactive side group such as lysine. Using a solid phase synthesis method, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is mixed with the solid support and reacted to form an amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently to yield the final desired peptide. The resultant linear peptides may then be reacted to form their corresponding cyclic peptides. Method for cyclizing peptides are known in the stand of the technique.

The term "pharmaceutically acceptable salts" refers to inorganic and organic acid addition salts of the compound. As used herein, the terms "pharmaceutically acceptable", "physiologically tolerable" and grammatical variations thereof, are used interchangeably and represent that the materials are capable of administration to or upon a mammal without the production of undesirable physiological effects such as nausea, dizziness, gastric upset and the like. Acids capable of forming salts with peptides include inorganic acids such as hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphersulfonic acid, china acid, mandelic acid, o-methylmandelic acid, hydrogen-benzenesulfonic acid, picric acid, adipic acid, D-o-tolyltartaric acid, tartronic acid, a-toluic acid, (o, m, p)-toluic acid, naphthylamine sulfonic acid, and other mineral or carboxylic acids well known to those skilled in the art. Preferred are trifluoroacetic acid (TFA), hydrochloric acid, perchloric acid, nitric acid, thiocyanic acid, sulfuric acid, phosphoric acid, acetic acid, propionic acid, oxalic acid, glycolic acid, lactic acid, pyruvic acid, malonic acid, succinic acid, maleic acid, fumaric acid, anthranilic acid, cinnamic acid, naphthalene sulfonic acid, sulfanilic acid or the like. More preferred are hydrochloric acid and trifluoracetic acid salts. The salts are prepared by contacting the free base form with a sufficient amount of the desired acid to produce a salt in the conventional manner.

Suitable bases capable of forming salts with the peptides of the present invention include inorganic bases such as sodium hydroxide and the like as well as organic bases such as mono-, di- and tri-alkyl and aryl amines (e.g., triethylamine, diisopropyl amine, methyl amine, dimethyl amine and the like) and optionally substituted ethanolamines (e.g. ethanolamine, diethanolamine, and the like).

The peptides of the invention preferably have been purified so as to be substantially free of contaminants. A material is said to be "substantially free of contaminants" if it has been substantially purified from undesired material with which it had been associated when synthesized, either in the cell or in an in vitro system, to a degree sufficient to make it useful for a desired purpose.

Pharmaceutical Compositions

An embodiment of the invention provides a pharmaceutical composition comprising the peptide consisting of the general sequence Xa-Leu-Gln-Gly-Xb (SEQ ID NO: 1), wherein Xa is selected from Pro-Gly, Gly and Ac-Gly and Xb is selected from Glu, and Glu-$NH_2$, and/or the pharmaceutically acceptable salts thereof, together with at least one pharmaceutically acceptable vehicle, excipient and/or diluent. A further embodiment of the invention provides a pharmaceutical composition comprising the peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, together with at least one pharmaceutically acceptable vehicle, excipient and/or diluent. A preferred embodiment of the invention provides a pharmaceutical composition comprising the peptide consisting of the general sequence Xa-Leu-Gln-Gly-Xb, wherein Xa is Ac-Gly and Xb is Glu (SEQ ID NO: 3), and/or the pharmaceutically acceptable salts thereof, together with at least one pharmaceutically acceptable vehicle, excipient and/or diluent. Another preferred embodiment of the invention provides a pharmaceutical composition comprising the peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, together with at least one pharmaceutically acceptable vehicle, excipient and/or diluent. Another preferred embodiment of the invention provides a pharmaceutical composition comprising the peptide consisting of the general sequence Xa-Leu-Gln-Gly-Xb, wherein Xa is Gly and Xb is Glu, and Glu binds to Gly to form the cyclic peptide (SEQ ID NO: 5):

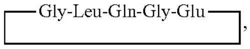, and/or the pharmaceutically acceptable salts thereof, together with at least one pharmaceutically acceptable vehicle, excipient and/or diluent.

Another preferred embodiment of the invention provides a pharmaceutical composition comprising the peptide consisting of the general sequence Xa-Leu-Gln-Gly-Xb, wherein Xa is Pro-Gly and Xb is Glu, and Pro binds to Glu to form the cyclic peptide (SEQ ID NO: 6):

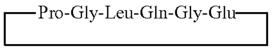

and/or the pharmaceutically acceptable salts thereof, together with at least one pharmaceutically acceptable vehicle, excipient and/or diluent.

More in particular the present invention is directed to a pharmaceutical composition comprising the peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$ and/or the pharmaceutically acceptable not-toxic salts thereof, together with at least one pharmaceutically acceptable vehicle, excipient and/or diluent. A further embodiment of the invention provides a pharmaceutical composition comprising the peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable not-toxic salts thereof, together with at least one pharmaceutically acceptable vehicle, excipient and/or diluent. A preferred embodiment of the invention provides a pharmaceutical composition comprising the peptide consisting of the general sequence Xa-Leu-Gln-Gly-Xb, wherein Xa is Ac-Gly and Xb is Glu (SEQ ID NO: 3), and/or the pharmaceutically acceptable not-toxic salts thereof, together with at least one pharmaceutically acceptable vehicle, excipient and/or diluent. Another preferred embodiment of the invention provides a pharmaceutical composition comprising the peptide consisting of the general sequence Xa-Leu-Gln-Gly-Xb, wherein Xa is Gly and Xb is Glu-$NH_2$ (SEQ ID NO: 4), and/or the pharmaceutically acceptable not-toxic salts thereof, together with at least one pharmaceutically acceptable vehicle, excipient and/or diluent. Another preferred embodiment of the invention provides a pharmaceutical composition comprising the peptide consisting of the general sequence Xa-Leu-Gln-Gly-Xb, wherein Xa is Gly and Xb is Glu, and Glu binds to Gly to form the cyclic peptide (SEQ ID NO: 5):

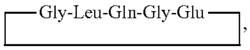, and/or the pharmaceutically acceptable not-toxic salts thereof, together with at least one pharmaceutically acceptable vehicle, excipient and/or diluent.

Another preferred embodiment of the invention provides a pharmaceutical composition comprising the peptide consisting of the general sequence Xa-Leu-Gln-Gly-Xb, wherein Xa is Pro-Gly and Xb is Glu, and Pro binds to Glu to form the cyclic peptide (SEQ ID NO: 6):

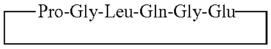

and/or the pharmaceutically acceptable not-toxic salts thereof, together with at least one pharmaceutically acceptable vehicle, excipient and/or diluent.

The pharmaceutical composition is designed to facilitate the administering a peptide of this invention in an effective manner. Generally a composition of this invention will have a peptide dissolved or dispersed in the pharmaceutically acceptable excipient.

Examples of suitable carriers or excipients include, without limitation, lactose, dextrose, sucrose, glucose, powdered sugar, sorbitol, mannitol, xylitol, starches, acacia gum, xanthan gum, guar gum, tara gum, mesquite gum, fenugreek gum, locust bean gum, ghatti gum, tragacanth gum, inositol, molasses, maltodextrin, extract of Irish moss, panwar gum, mucilage of isapol husks, Veegum, larch arabogalactan, calcium silicate, calcium phosphate, dicalcium phosphate, calcium sulfate, kaolin, sodium chloride, polyethylene glycol, alginates, gelatine, microcrystalline cellulose, polyvinylpyrrolidone, cellulose, water, saline, syrup, methylcellulose, ethylcellulose, hydroxypropylnethylcellulose, carboxymethylcellulose, polyacrylic acids such as Carbopols, such as Carbopol941, Carbopol980, Carbopol981, and gum bases such as Pharmagum™ (SPI Pharma Group; New Castle, Del.), and similar. Typically, the compositions of the present invention comprise from about 10% to about 90% by weight of the vehicle, the excipient or combinations thereof.

Preferably, the pharmaceutical composition contains from about 0.001% to about 90%, preferably from about 0.01% to about 75%, more preferably from about 0.1% to 50%, and still more preferably from about 0.1% to 10% by weight of a cyclic peptide of the present invention or a combination thereof, with the remainder consisting of suitable pharmaceutical carriers, excipients, and/or diluents.

The pharmaceutical composition can be formulated into powders, granules, tablets, capsules, suspensions, emulsions, syrups, oral dosage form, external preparation, suppository or in the form of sterile injectable solutions, such as aerosolized in a usual manner, respectively. When formulated, it can be prepared using a diluent or excipient such as generally used fillers, extenders, binders, wetting agents, disintegrating agents, surface active agents.

In the pharmaceutical composition, the solid preparation for oral administration may be a tablet, pill, powder, granule, or capsule. The solid preparation may further comprise an excipient. Excipients may be, for example, starch, calcium carbonate, sucrose, lactose, or gelatine. In addition, the solid preparation may further comprise a lubricant, such as magnesium stearate, or talc. In the pharmaceutical composition, liquid preparations for oral administration may be best suspensions, solutions, emulsions, or syrups. The liquid formulation may comprise water, or liquid paraffin. The liquid formulation may, for excipients, for example, include wetting agents, sweeteners, aromatics or preservatives. For the purposes of parenteral administration, compositions containing the peptides of the invention are preferably dissolved in distilled water and the pH preferably adjusted to about 6 to 8. If the peptide is to be provided in a lyophilized form, lactose can be added to the solution to facilitate the lyophilization process. In such form, the solution is then sterilized, introduced into vials and lyophilized.

Useful preparations of the compositions of the invention for parenteral administration also include sterile aqueous and non-aqueous solvents, suspensions and emulsions. Examples of useful non-aqueous solvents include propylene glycol, polyethylene glycol, vegetable oil, fish oil, and injectable organic esters.

Uses of the Peptides

"Excess accumulation of extracellular matrix" as used herein means the increased deposition of extracellular matrix components including, collagen, laminin, fibronectin and proteoglycans in tissue to an extent that results in impairment of tissue or organ function and ultimately, organ failure as a result of fibrotic disease. Extracellular matrix is a mixture of proteins, proteoglycans, glycoproteins and collagens assembled into a complex superstructure.

A variety of fibrotic conditions are characterized by excess accumulation of extracellular matrix. Such conditions include, for example, but are not limited to, glomerulonephritis, acute respiratory distress syndrome (ARDS), diabetes-associated pathologies such as diabetic kidney disease, kidney fibrosis, lung fibrosis, cardiac fibrosis, cardiac scarring, post infarction cardiac fibrosis, fibrotic diseases of the liver, liver fibrosis, liver cirrhosis, fibrosclerosis, myelofibrosis, and various types of cancer as reported below.

There are also a number of medical conditions associated with an excess accumulation of extracellular matrix. Such conditions include, for example, but are not limited to, post myocardial infarction, left ventricular hypertrophy, pulmonary fibrosis, veno-occlusive disease, post-spinal cord injury, post-retinal and glaucoma surgery, post-angioplasty restenosis and renal interstitial fibrosis, arteriovenous graft failure, arteriosclerosis, excessive scarring such as keloid scars, hypertrophic scars and scars resulting from injury, burns or surgery.

In the liver, almost all diseases lead to activation of the fibroblasts and production of matrix. This matrix then prevents the regeneration of the cells and disrupts the microarchitecture leading to functional deterioration and symptoms of increased portal pressure characteristic of liver failure. In the lung, the accumulation of matrix prevents adequate exchange of oxygen and carbon dioxide leading to chronic respiratory failure and in the most severe cases to asphyxiation. In the heart, the remodeling that takes place after ischemic attacks or in the context of cardiomyopathy leads to the development of a scar consisting of matrix that cannot contribute to heart muscle contraction and in the severe forms even expand instead of contracting thus leading to heart failure. In diabetic nephropathy, the accumulation of extracellular matrix in the functional units called glomeruli similarly leads to deterioration of kidney function.

The term "cancer" refers to any of various malignant neoplasms characterized by the proliferation of anaplastic cells that tend to disrupt organ function or invade surrounding tissue and metastasize to new body sites. It is known in the state of the art that cancer progression is associated with excess accumulation of extracellular matrix components and changes in extracellular matrix composition. Examples of different types of cancer suitable for treatment using the present invention include, but are not limited to, cancers of the breast, prostate, uterus, pancreas or colon, skin cancer, blood cell cancers such as lymphoma and leukemia, cancers of the central nervous system such as glioblastoma multiforme, fibroids, fibroma, fibroadenomas and fibrosarcomas.

As used herein preferred fibrotic conditions characterized by an excess accumulation of extracellular matrix in a tissue and/or an organ are selected from the group consisting of liver fibrosis, cirrhosis of the liver, lung fibrosis, chronic respiratory failure, cardiac fibrosis, ischemic heart disease, heart failure, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

From the state of the art it is known that a number of cytokines is involved in fibrotic processes. TGFβ is viewed as an important mediator of fibrosis and scar tissue, and it is also almost universally found in cancer suggesting its involvement in cancer growth and progression. TGFβ fibrogenic action results from simultaneous stimulation of matrix protein synthesis, inhibition of matrix degradation, and turnover. In fibrotic diseases overproduction of TGFβ results in excess accumulation of extracellular matrix which leads to tissue fibrosis and eventually organ failure. Fibrotic conditions associated with excessive extracellular matrix accumulation due to TGFβ overproduction are for example liver fibrosis, cirrhosis of the liver, lung fibrosis, chronic respiratory failure, cardiac fibrosis, heart failure, diabetic nephropathy, glomerulonephritis, various types of cancers.

Blocking the action of TGFβ with an agent such as an antibody has been shown to be therapeutic in fibrosis of different tissues, and to disrupt TGFβ overproduction. As used herein "inhibition of TGFβ" includes inhibition of TGFβ production resulting in overproduction and excess accumulation of extracellular matrix accumulation, regardless of the mechanism of TGFβ activity or overproduction, as well as inhibition of TGFβ activity, for example in causing excess deposition of extracellular matrix accumulation. This inhibition can be caused directly, e.g. by binding to TGFβ or its receptors, or can be caused indirectly, for example by inhibiting a pathway that results in TGFβ production, such as the integrin-pathway. Inhibition causes a reduction in the extracellular matrix accumulation producing activity of TGFβ regardless of the exact mechanism of inhibition.

A decrease in extracellular matrix production by other mechanisms either related to other cytokines or unrelated to any cytokine is also possible. In an attempt to find novel peptides as therapeutic to efficiently treat tissue fibrosis, the inventors have compared the activity of the peptides with sequences Gly-Leu-Hyp-Gly-Glu (GLOGE; SEQ ID NO: 12) and Gly-Leu-Asn-Gly-Glu (GLNGE; SEQ ID NO: 7) with Gly-Leu-Gln-Gly-Glu (GLQGE; SEQ ID NO: 2). GLNGE (SEQ ID NO: 7) is a short sequence contained in R1R2, which has been shown to diminish collagen accumulation; GLOGE (SEQ ID NO: 12) is a sequence known to be part of a sequence that binds to collagen-binding integrins.

Animal models of liver fibrosis are widely used to study the mechanisms underlying liver fibrosis and the effect of various drugs on its progression. Hepatic fibrosis is characteristic of acute or chronic injury to the liver in response to diverse metabolic, viral, and toxic stimuli. Excessive deposition of extracellular matrix accumulation proteins, including hyaluronic acid, laminin, and collagen occur during fibrogenesis along with activation of hepatic stellate cells (HSCs). Activated HSCs produce transforming growth factor TGFβ, which induces collagen production that leads to extracellular matrix accumulation, and they also up-regulate tissue inhibitors of metalloproteinases. $CCl_4$ is a laboratory reagent characterized by toxicity causing acute liver damage and liver fibrosis and is extensively used in liver-related studies. It is well known in the state of the art, that intraperitoneal administration of $CCl_4$ induces liver damage and concomitantly, production and release of TGFβ, which in turn enhances synthesis of liver collagen type I, III and IV mRNA and protein; accordingly, it has been shown that in vivo neutralization of TGFβ reduces collagen mRNA.

The experiments conducted on $CCl_4$ induced liver fibrosis in mice (Example 2, FIG. 1 and Example 3, FIG. 2) have shown that the linear peptides of sequence Gly-Leu-Gln-Gly-Glu-$NH_2$ and Ac-Gly-Leu-Gln-Gly-Glu were able to inhibit collagen deposition. Surprisingly, the inhibitory activity of Gly-Leu-Gln-Gly-Glu-$NH_2$ (Linear GLQGE-$NH_2$) and of Ac-Gly-Leu-Gln-Gly-Glu (Linear Ac-GLQGE) was stronger compared to the correspondent acetylated or amidated form of the controls Gly-Leu-Hyp-Gly-Glu (Linear GLOGE) and Gly-Leu-Asn-Gly-Glu (Linear GLNGE).

This finding is supported by the observation that the linear sequence Gly-Leu-Gln-Gly-Glu-$NH_2$ (Linear GLQGE-$NH_2$; SEQ ID NO: 4) efficiently inhibits unstimulated TGFβ expression in murine hepatocytes (data not shown), whereas the linear sequences of two controls: Gly-Leu-Asn-Gly-Glu-$NH_2$ (GLNGE-$NH_2$; SEQ ID NO: 9) and Gly-Leu-Hyp-Gly-Glu-$NH_2$ (GLOGE-$NH_2$; SEQ ID NO: 14) had no effect.

Moreover, the cyclic peptide Gly-Leu-Gln-Gly-Glu (cyclic GLQGE; SEQ ID NO: 5) had a larger inhibitory effect compared to the linear Gly-Leu-Gln-Gly-Glu-$NH_2$ (SEQ ID NO: 4) or Ac-Gly-Leu-Gln-Gly-Glu (SEQ ID NO: 3) on collagen accumulation in chemically induced chronic liver damage in mice (FIG. 1). Similarly to the linear peptides, the cyclic Gly-Leu-Asn-Gly-Glu (cyclic GLNGE; SEQ ID NO: 10) and Gly-Leu-Hyp-Gly-Glu (cyclic GLOGE; SEQ ID NO: 15) failed to inhibit collagen accumulation.

Thus, it seems that the peptides with sequence Gly-Leu-Gln-Gly-Glu (SEQ ID NO: 2) in both linear and cyclic form are more able than both Gly-Leu-Asn-Gly-Glu (SEQ ID NO: 7) and Gly-Leu-Hyp-Gly-Glu (SEQ ID NO: 12) sequences to inhibit collagen accumulation in chemically induced liver damage, and could be used as therapeutics to inhibit fibrosis progression.

In particular both cyclic peptides Gly-Leu-Gln-Gly-Glu (SEQ ID NO: 5) and Pro-Gly-Leu-Gln-Gly-Glu (SEQ ID NO: 6) (FIG. 2) had a strong inhibitory effect on collagen accumulation, and are thus considered of particular interest as therapeutic agent. Indeed, cyclic peptides have the advantage over the linear peptides to be resistant to hydrolysis by exopeptidases due to the lack of both amino and carboxyl termini, and resistant even to endopeptidases, as the structure is less flexible than linear peptides. In particular, cyclic peptides work very well as receptor agonists or antagonists because of their structural rigidity. Moreover, compared to small molecules such as antibodies, they can be more selective while the size of molecule can be smaller and therefore more advantageous. The cyclic peptide Gly-Leu-Gin-Gly-Glu (SEQ ID NO: 5) was also able to diminish collagen accumulation in an experimental model of lung fibrosis (FIG. 4), confirming the ability of this peptide to decrease the build-up of matrix and suggesting that it is effective in other diseases associated with increased extracellular matrix amount.

Therefore, the present invention provides a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof for use in the treatment of a fibrotic condition characterized by an excess accumulation of extracellular matrix in a tissue and/or an organ. In a particular embodiment, the present invention provides a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, for use in the treatment of a fibrotic condition characterized by an excess accumulation of extracellular matrix in a tissue and/or an organ. In a preferred embodiment, the present invention provides a peptide consisting of the general sequence Xa-Leu-Gln-Gly-Xb, wherein Xa is Ac-Gly and Xb is Glu (SEQ ID NO: 3), and/or the pharmaceutically acceptable salts thereof, for use in the treatment of a fibrotic condition characterized by an excess accumulation of extracellular matrix in a tissue and/or an organ. In a preferred embodiment, the present invention provides a peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, for use in the treatment of a fibrotic condition characterized by an excess accumulation of extracellular matrix in a tissue and/or an organ. In a preferred aspect, the present invention provides a peptide consisting of the general sequence Xa-Leu-Gln-Gly-Xb, wherein Xa is Gly and Xb is Glu, and Glu binds to Gly to form the cyclic peptide (SEQ ID NO: 5):

Gly-Leu-Gln-Gly-Glu , and/or the pharmaceutically acceptable salts thereof, for use in the treatment of a fibrotic condition characterized by an excess accumulation of extracellular matrix in a tissue and/or an organ. In a more preferred aspect, the present invention provides a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

Pro-Gly-Leu-Gln-Gly-Glu , and/or the pharmaceutically acceptable salts thereof, for use in the treatment of a fibrotic condition characterized by an excess accumulation of extracellular matrix in a tissue and/or an organ.

The cyclic peptides disclosed herein were also able to prevent growth of various types of cancers. Indeed, the cyclic peptide Gly-Leu-Gln-Gly-Glu (SEQ ID NO: 5) (HCl salt) was significantly able to diminish melanoma cancer size in mice (FIG. 3). Moreover, the cyclic peptide Gly-Leu-Gln-Gly-Glu (SEQ ID NO: 5) (HCl salt) was able to diminish the growth of breast cancer in mice (FIG. 5).

A preferred embodiment of the present invention provides a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof, for use in treatment of a fibrotic condition characterized by an excess accumulation of extracellular matrix in a tissue and/or an organ, wherein said condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas. In a particular embodiment, the present invention provides a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, for use in treatment of a fibrotic condition characterized by an excess accumulation of extracellular matrix in a tissue and/or an organ, wherein said condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas. In a preferred embodiment, the present invention provides a peptide consisting of the general sequence Xa-Leu-Gln-Gly-Xb, wherein Xa is Ac-Gly and Xb is Glu (SEQ ID NO: 3), and/or the pharmaceutically acceptable salts thereof, for use in treatment of a fibrotic condition characterized by an excess accumulation of extracellular matrix in a tissue and/or an organ, wherein said condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas. In a preferred embodiment, the present invention provides a peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, for use in treatment of a fibrotic condition characterized by an excess accumulation of extracellular matrix in a tissue and/or an organ, wherein said condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas. In a preferred aspect, the present invention provides a peptide consisting of the general sequence Xa-Leu-Gln-Gly-Xb, wherein Xa is Gly and Xb is Glu, and Glu binds to Gly to form the cyclic peptide (SEQ ID NO: 5):

Gly-Leu-Gln-Gly-Glu, and/or the pharmaceutically acceptable salts thereof, for use in treatment of a fibrotic condition characterized by an excess accumulation of extracellular matrix in a tissue and/or an organ, wherein said condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas. In a more preferred aspect, the present invention provides a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

Pro-Gly-Leu-Gln-Gly-Glu, and/or the pharmaceutically acceptable salts thereof, for use in treatment of a fibrotic condition characterized by an excess accumulation of extracellular matrix in a tissue and/or an organ, wherein said condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

The peptides or the pharmaceutical compositions disclosed herein may be administered by a variety of routes to a subject such as a mammal, including rats, mice, dogs, cattle, horses, monkeys, and humans.

The peptides disclosed herein can be suspended in physiologically compatible pharmaceutical carriers, such as physiological saline, phosphate-buffered saline, or the like to form physiologically acceptable aqueous pharmaceutical compositions for administration to a subject. Parenteral vehicles include sodium chloride solution, Ringer's dextrose, dextrose and sodium chloride and lactated Ringer's solution. Other substances may be added a desired, such as antimicrobials.

Administration method of the peptides disclosed herein are those known in the art for therapeutic agents and may be, for example, intravenous, intraperitoneal, intramuscular, intradermal, and epidermal including subcutaneous and intradermal, oral, or applied to mucosal surfaces, e.g. by intranasal administration using inhalation of aerosol suspensions, and by implanting to muscle or other tissue in the subject. Suppositories and topical preparations are also contemplated.

In general, if it is desired to increase the absorption of the peptide of this invention through ocular, buccal, transdermal, rectal, nasal inhalation or oral inhalation to employ certain penetration enhancers. These enhancers can include chelators such as EDTA, citric acid, N-acyl derivatives of collagen, enamines (N-amino-N-acyl derivatives of β-diketones). Surfactants can also be used to enhance penetration. These include sodium lauryl sulfate, polyoxyethylene-9-lauryl ether and polyoxyethelene-20-cetyl ether. Bile salts and derivatives are also known to enhance the penetration of peptides and these include, sodium deoxycholate, sodium glycocholate, sodium taurocholate, sodium taurodihydrofusidate and sodium glycodihyrofusidate. Still another type of penetration enhancer useful in the composition of this invention includes certain fatty acids and derivatives such as oleic acid, caprylic acid, capric acid, acylcarnitines, acylcholine and mono and diglycerides. Nonsurfactants are also useful as penetration enhancers. The penetration enhancers can be used in the solution with the compounds of this invention where the compound and the penetration enhancers are in a pharmaceutically acceptable sterile solution which can be administered, for example by nasal administration. Alternatively the penetration enhancers can be included in a powered formulation that can be administered as an aerosol by suspending the particulate matter in the stream of air and having the patient inhale the suspended particles. Such powered formulations can be administered by a dry-powder inhaler.

Thus the peptide compounds of the invention may be administered by human health professionals as well as veterinarians.

Another related aspect of the invention is a method for administering a compound of this invention, in conjunction with other therapies such as conventional drug therapy chemotherapy directed against cancer and for control of establishment of metastases. The administration of a peptide of this invention is typically conducted before, during or after chemotherapy.

The term "therapeutically effective amount" refers to the amount of a linear or cyclic peptide, as well as of the pharmaceutical composition disclosed herein that is capable of achieving a therapeutic effect in a subject in need thereof. For example, a therapeutically effective amount of a cyclic peptide or a combination of cyclic peptides can be the amount that is capable of preventing or reduce excess accumulation of extracellular matrix in susceptible tissues and organs, or of one or more associated symptoms.

One of ordinary skill will recognize that the potency, and therefore a "therapeutically effective" amount can vary for the compounds of this invention. However, as shown by this specification one skilled in the art can readily assess the potency of a candidate peptide of this invention. Potency can be measured by a variety of means including inhibition of TGFβ production, collagen accumulation, inhibition of cell adhesion to vitronectin, fibronectin and/or collagen, and the like assays.

A therapeutically effective amount of a peptide or of the pharmaceutical composition of this invention is typically an amount of peptide such that when administered in a physiologically tolerable composition is sufficient to achieve a plasma concentration of from about 0.1 nanogram (ng) per milliliter (ml) to about 200 μg/ml, preferably from about 1 ng/ml to about 100 μg/ml. The dosage per body weight can vary from 10 mg/kg to 100 mg/kg, preferably from 20 mg/kg to 80 mg/kg, more preferably from 20 mg/kg to 60 mg/kg, and still more preferably from 20 mg/kg to 40 mg/kg, in one or more dose administrations daily, for one or several days.

The preferred dosage regimen and mode of administration of the peptides or of the pharmaceutical compositions of the present invention may vary depending on the severity of the accumulation of extracellular matrix and on the resulting impairment of tissue or organ function, the subject's health, previous medical history, age, weight, height, sex and response to treatment and the judgment of the treating physician. The preferred dosage regimen and mode of administration may be suitably selected by those skilled in the art. Initially, such parameters are readily determined by skilled practitioners using appropriate testing in animal models for safety and efficacy, and in human subjects during clinical trials of candidate therapeutic formulations. Suitable animal models of human fibrotic conditions are known in the art.

After administration, the efficacy of the therapy using the methods of the invention is assessed by various methods including biopsy of kidney, lung or liver or another tissue target by excess matrix accumulation to detect the amount of extracellular matrix accumulated. An absence of significant excess accumulation of extracellular matrix, or a decrease in the amount or expansion of extracellular matrix in the tissue or organ will indicate the desired therapeutic response in the subject. Preferably, a non-invasive procedure is used to detect a therapeutic response. For example, changes in TGFβ activity can be measured in plasma samples before and after treatment with a therapeutic compound, and biopsy tissue can be used to individually isolate diseased tissues which are then used for RNA isolation. mRNA transcripts for TGFβ, and/or extracellular matrix components (e.g. collagen) are then determined using reverse transcriptase-polymerase chain reaction (RT-PCR).

"Administering" or "administration" includes but is not limited to delivery by an injectable form, such as, for example, an intravenous, intramuscular, intradermal or subcutaneous route or mucosal route, for example, as a nasal spray or aerosol for inhalation or as an ingestable solution, capsule or tablet.

"Reducing the excess accumulation of extracellular matrix" means preventing excess accumulation of extracellular matrix, e.g. in tissue, organs or at a wound site, preventing further deposition of extracellular matrix and/or decreasing the amount of excess accumulated matrix already present, to maintain or restore tissue or organ function or appearance.

Moreover, according to a preferred embodiment, the present invention also provides a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gin-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment.

According to a still more preferred embodiment, the present invention provides a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof, wherein the accumulation of extracellular matrix in said tissue and/or organ is prevented or reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

Another embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment.

Another preferred embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas . . .

A further embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Ac-Gly and Xb is Glu (SEQ ID NO: 3), and/or the pharmaceutically acceptable salts thereof, and wherein the accumulation of extracellular matrix in said tissue and/or organ is reduced from the level existing at the time of treatment, A further preferred embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Ac-Gly and Xb is Glu (SEQ ID NO: 3), and/or the pharmaceutically acceptable salts thereof, wherein the accumulation of extracellular matrix in said tissue and/or organ is reduced from the level existing at the time of treatment, and wherein the fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

A further embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, and wherein the accumulation of extracellular matrix in said tissue and/or organ is reduced from the level existing at the time of treatment, A further preferred embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, wherein the accumulation of extracellular matrix in said tissue and/or organ is reduced from the level existing at the time of treatment, and wherein the fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

A further embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Gly and Xb is Glu, and Glu binds to Gly to form the cyclic peptide (SEQ ID NO: 5):

Gly-Leu-Gln-Gly-Glu, and/or the pharmaceutically acceptable salts thereof, wherein the accumulation of extracellular matrix in said tissue and/or organ is reduced from the level existing at the time of treatment, A further preferred embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Gly and Xb is Glu, and Glu binds to Gly to form the cyclic peptide (SEQ ID NO: 5):

Gly-Leu-Gln-Gly-Glu, and/or the pharmaceutically acceptable salts thereof, wherein the accumulation of extracellular matrix in said tissue and/or organ is reduced from the level existing at the time of treatment, and wherein the fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

A further embodiment of the present invention relates to a method for the treatment of a fibrotic condition characterized by an excess accumulation of extracellular matrix in a tissue and/or an organ, comprising administering to a patient a therapeutically effective amount of a consisting of the general sequence Xa-Leu-Gln-Gly-Xb, wherein Xa is Pro-Gly and Xb is Glu, and Pro binds to Glu to form the cyclic peptide (SEQ ID NO: 6):

Pro-Gly-Leu-Gln-Gly-Glu, and/or the pharmaceutically acceptable salts thereof, wherein the accumulation of extracellular matrix in said tissue and/or organ is reduced from the level existing at the time of treatment, A further preferred embodiment of the present invention relates to a method for the treatment of a fibrotic condition characterized by an excess accumulation of extracellular matrix in a tissue and/or an organ, comprising administering to a patient a therapeutically effective amount of a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

Pro-Gly-Leu-Gln-Gly-Glu, and/or the pharmaceutically acceptable salts thereof, wherein the accumulation of extracellular matrix in said tissue and/or organ is reduced from the level existing at the time of treatment, and wherein the fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

In another embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising the peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment.

In another preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising the peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Ac-Gly and Xb is Glu (SEQ ID NO: 3), and/or the pharmaceutically acceptable salts thereof, and wherein the accumulation of extracellular matrix in said tissue and/or organ is reduced from the level existing at the time of treatment.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, and wherein the accumulation of extracellular matrix in said tissue and/or organ is reduced from the level existing at the time of treatment. In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Gly and Xb is Glu, and Glu binds to Gly to form the cyclic peptide (SEQ ID NO: 5):

Gly-Leu-Gln-Gly-Glu, and/or the pharmaceutically acceptable salts thereof, and wherein the accumulation of extracellular matrix in said tissue and/or organ is reduced from the level existing at the time of treatment.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

Pro-Gly-Leu-Gln-Gly-Glu, and/or the pharmaceutically acceptable salts thereof, and wherein the accumulation of extracellular matrix in said tissue and/or organ is reduced from the level existing at the time of treatment.

In another embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising the peptide consisting of the general sequence Xa-Leu-Gin-Gly-Xb (SEQ ID NO: 1), wherein Xa is selected from Pro-Gly, Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

In another preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising the peptide consisting of the general sequence Xa-Leu-Gln-Gly-Xb (SEQ ID NO: 1), wherein Xa is selected from Gly and Ac-Gly and Xb is selected from Glu and Glu-$NH_2$, and/or the pharmaceutically acceptable salts thereof, wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Ac-Gly and Xb is Glu (SEQ ID NO: 3), and/or the pharmaceutically acceptable salts thereof, and wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Gly and Xb is Glu-$NH_2$ (SEQ ID NO: 4), and/or the pharmaceutically acceptable salts thereof, and wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Gly and Xb is Glu, and Glu binds to Gly to form the cyclic peptide (SEQ ID NO: 5):

Gly-Leu-Gln-Gly-Glu (cyclic), and/or the pharmaceutically acceptable salts thereof, and wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

In a further preferred embodiment, the present invention provides a method for the treatment of a fibrotic condition characterized by an excess accumulation of extracellular matrix in a tissue and/or an organ, comprising administering to a patient a therapeutically effective amount of a pharmaceutical composition comprising a peptide consisting of the general sequence Xa-Leu-Gln-Gly-Xb, wherein Xa is Pro-Gly and Xb is Glu, and Pro binds to Glu to form the cyclic peptide (SEQ ID NO: 6):

Pro-Gly-Leu-Gln-Gly-Glu (cyclic), and/or the pharmaceutically acceptable salts thereof, and wherein the accumulation of extracellular matrix in said tissue and/or organ is reduced from the level existing at the time of treatment, and wherein said fibrotic condition is selected from the group consisting of liver fibrosis, cirrhosis of the liver, lung fibrosis, chronic respiratory failure, cardiac fibrosis, heart failure, ischemic heart disease, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

Figure 1:
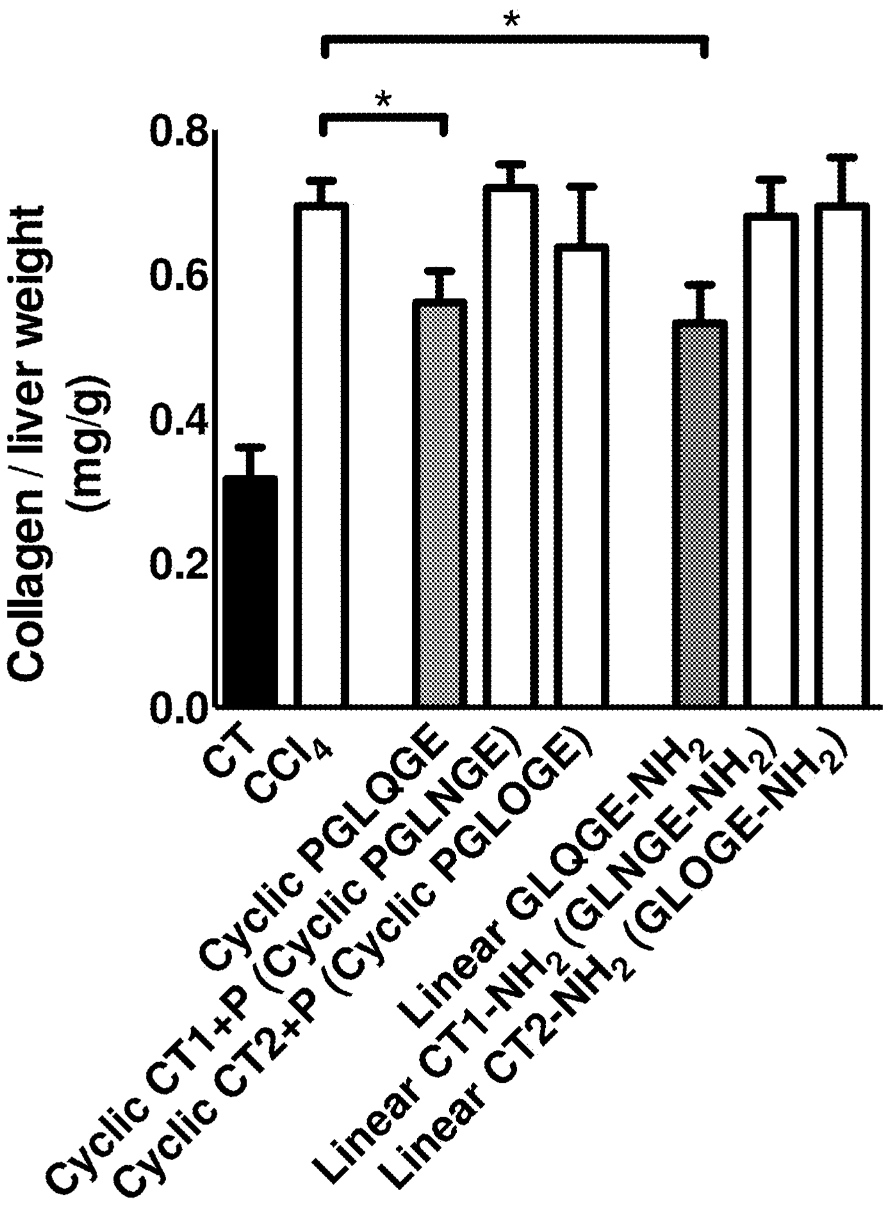
FIG. 1 Prevention of fibrosis progression by proline-containing cyclic and amidated linear peptides. Mice were injected for 6 weeks with $CCl_4$ in order to induce liver fibrosis. Starting on day 32 the mice received daily intraperitoneal injections of 25 mg/kg/mouse/day of the peptides in 0.9% NaCl for a total of 10 days. $CCl_4$-treated mice also received NaCl 0.9%. The healthy control group (CT) only received 0.9% NaCl. N=4/10/Aug. 5, 2010/8/11/7 in two experiments. The following peptides were tested on $CCl_4$-treated mice: cyclic Pro-Gly-Leu-Gln-Gly-Glu (Cyclic PGLQGE; SEQ ID NO: 6), and compared to two controls: cyclic Pro-Gly-Leu-Asn-Gly-Glu (Cyclic CT1+P: cyclic PGLNGE; SEQ ID NO: 11) and cyclic Pro-Gly-Leu-Hyp-Gly-Glu (Cyclic CT2+P: cyclic PGLOGE; SEQ ID NO: 16). Linear Gly-Leu-Gln-Gly-Glu-$NH_2$ (Linear GLQGE-$NH_2$; SEQ ID NO: 4) was also tested and compared to two controls: linear Gly-Leu-Asn-Gly-Glu-$NH_2$ (Linear CT1—$NH_2$: linear GLNGE-$NH_2$; SEQ ID NO: 9) and linear Gly-Leu-Hyp-Gly-Glu-$NH_2$ (Linear CT2—$NH_2$: linear GLOGE-$NH_2$; SEQ ID NO: 14). * $p<0.05$. Evaluated by t-test. Data presented as mean+SEM.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

Example 1: Peptide Synthesis

The peptide Gly-Leu-Gln-Gly-Glu (GLQGE; SEQ ID NO: 2) was synthesized in linear form as Gly-Leu-Gln-Gly-Glu-$NH_2$ (also named linear GLQGE-$NH_2$; SEQ ID NO: 4) and in linear form as acetate-Gly-Leu-Gln-Gly-Glu (also named linear Ac-GLOGE; SEQ ID NO: 3) and in cyclic form as cyclic Gly-Leu-Gln-Gly-Glu (also named cyclic GLQGE (SEQ ID NO: 5) without C-terminal amide and without N-terminal acetate). The peptide Pro-Gly-Leu-Gln-Gly-Glu (also named cyclic PGLOGE; SEQ ID NO: 6) was only synthesized in cyclic form. Both control peptides Gly-Leu-Asn-Gly-Glu (also named as Linear CT1 (Linear GLNGE); SEQ ID NO: 7) and Gly-Leu-Hyp-Gly-Glu (also named as Linear CT2 (Linear GLOGE); SEQ ID NO: 12) were synthesized in linear form with C-terminal amidation (GLNGE-$NH_2$ (SEQ ID NO: 9) and GLOGE-$NH_2$ (SEQ ID NO: 14)) and with N-terminal acetylation (Ac-GLNGE (SEQ ID NO: 8) and Ac-GLOGE (SEQ ID NO: 13)) and also in cyclic form with and without proline (cyclic GLNGE (SEQ ID NO: 10) or cyclic PGLNGE (SEQ ID NO: 11) as well as cyclic GLOGE (SEQ ID NO: 15) or cyclic PGLOGE (SEQ ID NO: 16)). The designation of all peptides used in the present application are listed in Table 1.

The linear peptides were synthesized on an ABI 433 peptide synthesizer (Life Technologies) using standard Fmoc (N-(9-fluorenyl) methoxycarbonyl) chemistry on Rink amide resin (Merck KGaA). Peptide purification was by RP-HPLC. Purity and identity of the peptides were verified by RP-HPLC and ESI-TOF mass spectrometry. Cyclic peptide Gly-Leu-Gln-Gly-Glu (SEQ ID NO: 5) was synthesized where Glu binds to Gly directly (head to tail cyclization) and $H_2O$ is removed or in the presence of proline. The cyclic peptide with proline in the ring was synthesized as fully protected peptides on TCP resin (Intavis Bioanalytical Instruments AG) and cyclized using propylphosphonic anhydride. The cyclic peptides without proline were synthesized using the liquid phase synthesis. All the groups were protected by protective groups, leaving only the N-terminal amino group and C-terminal carboxyl group. After the ring was formed in the liquid phase, the protective groups were removed. In this case, no TCP resin, and no propylphosphonic anhydride were used.

Table 1 reports the peptides used in the present invention and the corresponding SEQ ID NOs in the sequence listing.

Linear Ac-GLQGE (Ac-Gly-Leu-Gln-Gly-Glu) (SEQ ID NO: 3)

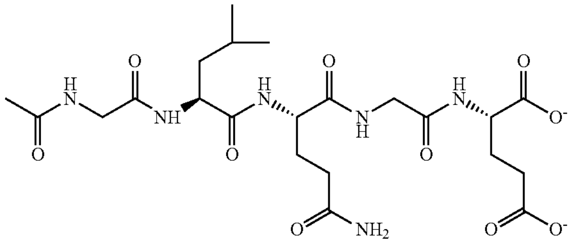

TABLE 1

| Peptide sequence | Form | Designation | SEQ ID NO |
|---|---|---|---|
| Xa-Leu-Gln-Gly-Xb | — | general sequence | 1 |
| Gly-Leu-Gln-Gly-Glu | linear | Linear GLQGE | 2 |
| Ac-Gly-Leu-Gln-Gly-Glu | linear | Linear Ac-GLQGE | 3 |
| Gly-Leu-Gln-Gly-Glu-$NH_2$ | linear | Linear GLQGE-$NH_2$ | 4 |
| Gly-Leu-Gln-Gly-Glu | cyclic | Cyclic GLQGE | 5 |
| Pro-Gly-Leu-Gln-Gly-Glu | cyclic | Cyclic PGLQGE | 6 |
| Gly-Leu-Asn-Gly-Glu | linear | Linear CT1 (GLNGE) | 7 |
| Ac-Gly-Leu-Asn-Gly-Glu | linear | Linear Ac-CT1 (Ac-GLNGE) | 8 |
| Gly-Leu-Asn-Gly-Glu-$NH_2$ | linear | Linear CT1-$NH_2$ (GLNGE-$NH_2$) | 9 |
| Gly-Leu-Asn-Gly-Glu | cyclic | Cyclic CT1 (Cyclic GLNGE) | 10 |
| Pro-Gly-Leu-Asn-Gly-Glu | cyclic | Cyclic CT1+P (Cyclic PGLNGE) | 11 |
| Gly-Leu-Hyp-Gly-Glu | linear | Linear CT2 (GLOGE) | 12 |
| Ac-Gly-Leu-Hyp-Gly-Glu | linear | Linear Ac-CT2 (Ac-GLOGE) | 13 |
| Gly-Leu-Hyp-Gly-Glu-$NH_2$ | linear | Linear CT2-$NH_2$ (GLOGE-$NH_2$) | 14 |
| Gly-Leu-Hyp-Gly-Glu | cyclic | Cyclic CT2 (Cyclic GLOGE) | 15 |
| Pro-Gly-Leu-Hyp-Gly-Glu | cyclic | Cyclic CT2+P (Cyclic PGLOGE) | 16 |

Linear GLQGE (Gly-Leu-Gln-Gly-Glu) (SEQ ID NO: 2)

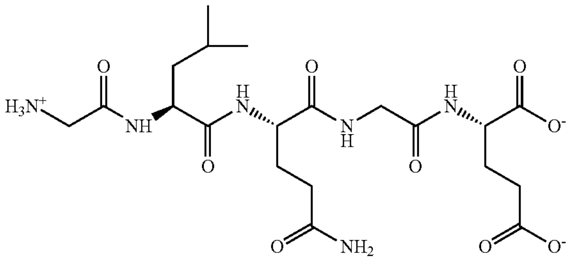 [SMILES: CC(C)C[C@H](NC(=O)C[NH3+])C(=O)N[C@@H](CCC(N)=O)C(=O)NCC(=O)N[C@@H](CCC(=O)[O-])C(=O)[O-]]

Linear GLQGE-$NH_2$ (Gly-Leu-Gln-Gly-Glu-$NH_2$) (SEQ ID NO: 4)

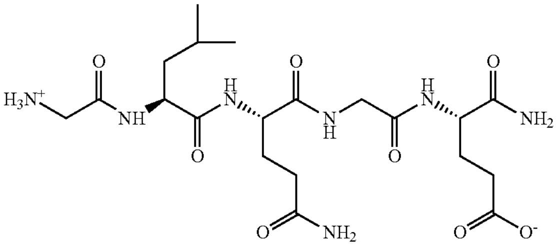 [SMILES: CC(C)C[C@H](NC(=O)C[NH3+])C(=O)N[C@@H](CCC(N)=O)C(=O)NCC(=O)N[C@@H](CCC(=O)[O-])C(N)=O]

Cyclic GLQGE (SEQ ID NO: 5)
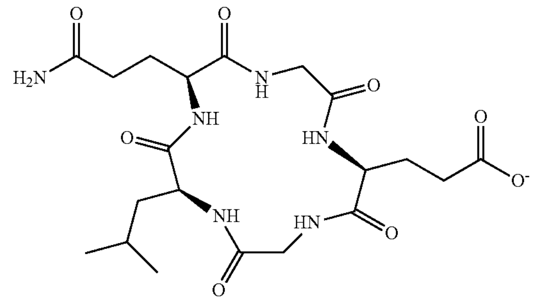 [SMILES: CC(C)C[C@@H]1NC(=O)CNC(=O)[C@H](CCC(=O)[O-])NC(=O)CNC(=O)[C@H](CCC(N)=O)NC1=O]
Cyclic PGLQGE (SEQ ID NO: 6)
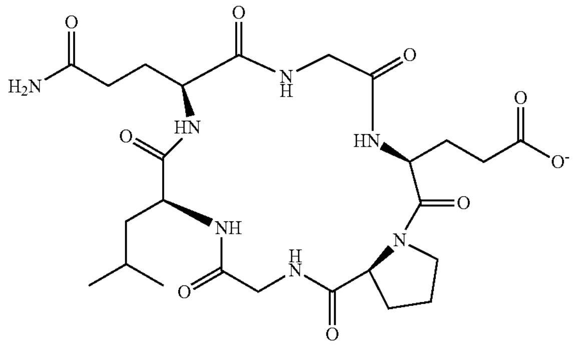 [SMILES: CC(C)C[C@@H]1NC(=O)CNC(=O)[C@@H]2CCCN2C(=O)[C@H](CCC(=O)[O-])NC(=O)CNC(=O)[C@H](CCC(N)=O)NC1=O]
Linear CT1 (Gly-Leu-Asn-Gly-Glu) (SEQ ID NO: 7)
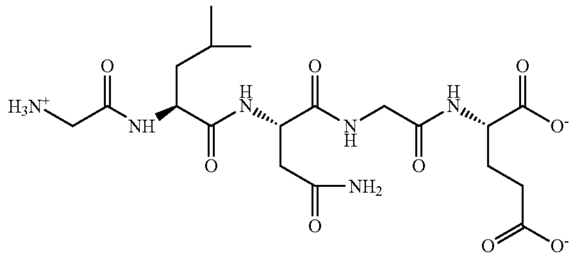 [SMILES: CC(C)C[C@H](NC(=O)C[NH3+])C(=O)N[C@@H](CC(N)=O)C(=O)NCC(=O)N[C@@H](CCC(=O)[O-])C(=O)[O-]]
Linear CT1—$NH_2$ (Gly-Leu-Asn-Gly-Glu-$NH_2$) (SEQ ID NO: 9)
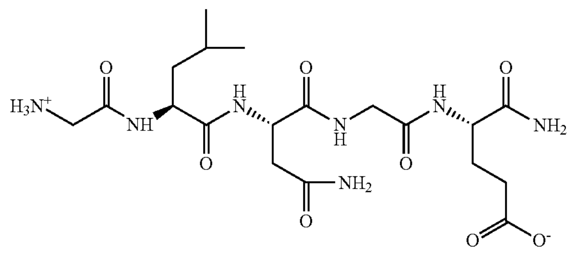 [SMILES: CC(C)C[C@H](NC(=O)C[NH3+])C(=O)N[C@@H](CC(N)=O)C(=O)NCC(=O)N[C@@H](CCC(=O)[O-])C(N)=O]
Linear Ac-CT1 (Ac-Gly-Leu-Asn-Gly-Glu) (SEQ ID NO: 8)
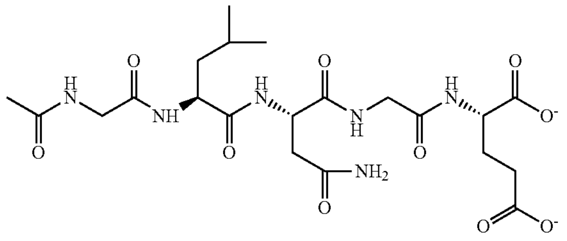 [SMILES: CC(=O)NCC(=O)N[C@@H](CC(C)C)C(=O)N[C@@H](CC(N)=O)C(=O)NCC(=O)N[C@@H](CCC(=O)[O-])C(=O)[O-]]
Cyclic CT1 (Gly-Leu-Asn-Gly-Glu) (SEQ ID NO: 10)
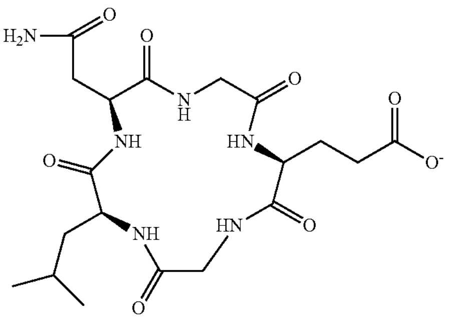 [SMILES: CC(C)C[C@@H]1NC(=O)CNC(=O)[C@H](CCC(=O)[O-])NC(=O)CNC(=O)[C@H](CC(N)=O)NC1=O]
Cyclic CT1+P (Pro-Gly-Leu-Asn-Gly-Glu) (SEQ ID NO: 11)
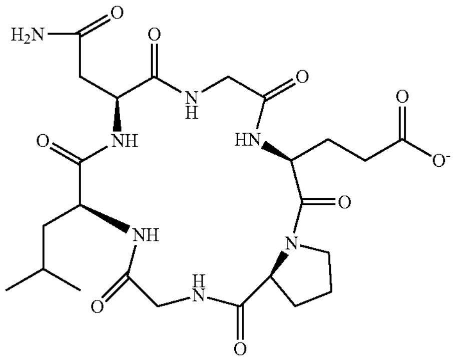 [SMILES: CC(C)C[C@@H]1NC(=O)CNC(=O)[C@@H]2CCCN2C(=O)[C@H](CCC(=O)[O-])NC(=O)CNC(=O)[C@H](CC(N)=O)NC1=O]
Linear CT2 (Gly-Leu-Hyp-Gly-Glu) (SEQ ID NO: 12)
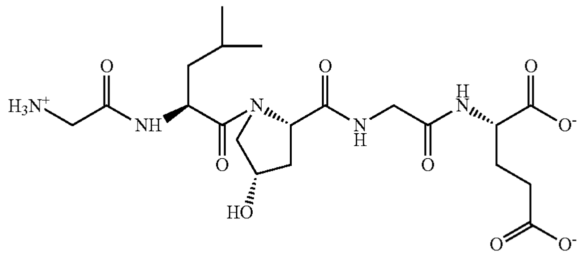 [SMILES: CC(C)C[C@H](NC(=O)C[NH3+])C(=O)N1C[C@@H](O)C[C@H]1C(=O)NCC(=O)N[C@@H](CCC(=O)[O-])C(=O)[O-]]

Linear CT2-$NH_2$ (Gly-Leu-Hyp-Gly-Glu-$NH_2$) (SEQ ID NO: 14)

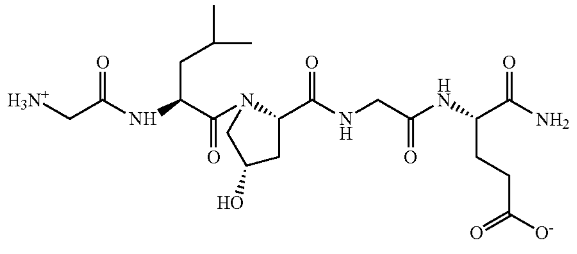 [SMILES: CC(C)C[C@H](NC(=O)C[NH3+])C(=O)N1C[C@@H](O)C[C@H]1C(=O)NCC(=O)N[C@@H](CCC(=O)[O-])C(N)=O]

Linear Ac-CT2 (Ac-Gly-Leu-Hyp-Gly-Glu) (SEQ ID NO: 13)

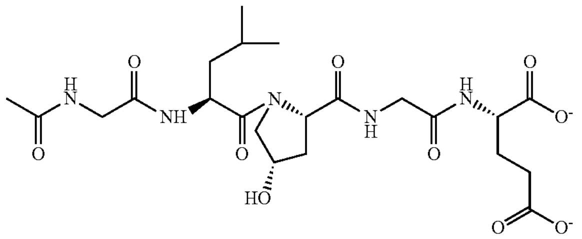 [SMILES: CC(=O)NCC(=O)N[C@@H](CC(C)C)C(=O)N1C[C@@H](O)C[C@H]1C(=O)NCC(=O)N[C@@H](CCC(=O)[O-])C(=O)[O-]]

Cyclic CT2 (Gly-Leu-Hyp-Gly-Glu) (SEQ ID NO: 15)

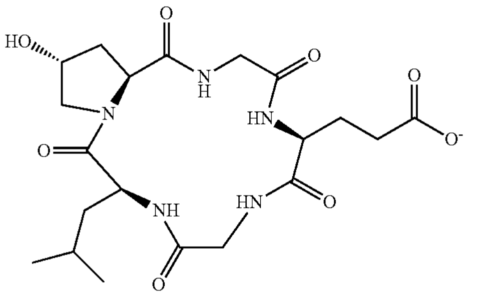 [SMILES: CC(C)C[C@@H]1NC(=O)CNC(=O)[C@H](CCC(=O)[O-])NC(=O)CNC(=O)[C@@H]2C[C@@H](O)CN2C1=O]

Cyclic CT2+P (Pro-Gly-Leu-Hyp-Gly-Glu) (SEQ ID NO: 16)

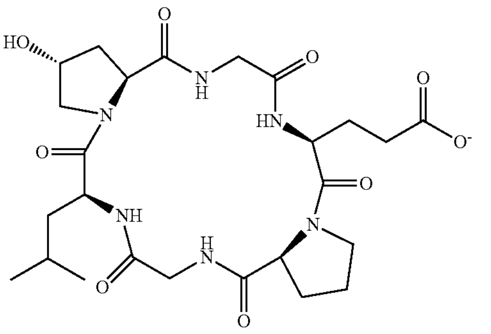 [SMILES: CC(C)C[C@@H]1NC(=O)CNC(=O)[C@@H]2CCCN2C(=O)[C@H](CCC(=O)[O-])NC(=O)CNC(=O)[C@@H]2C[C@@H](O)CN2C1=O]

Example 2: Effect of cyclic peptides with proline and amidated linear peptides on chemically induced liver fibrosis in mice.

Mice were injected for 6 weeks with $CCl_4$ in order to induce liver fibrosis. Starting on day 32 the mice received daily intraperitoneal injections of the peptides at a final dose of 25 mg/kg/mouse/day diluted in NaCl 0.9% for a total of 10 days. In these experiments, the following peptides were tested: cyclic peptide Pro-Gly-Leu-Gln-Gly-Glu (SEQ ID NO: 6), cyclic peptide Pro-Gly-Leu-Asn-Gly-Glu (SEQ ID NO: 11), cyclic peptide Pro-Gly-Leu-Hyp-Gly-Glu (SEQ ID NO: 16), linear peptide Gly-Leu-Gln-Gly-Glu-$NH_2$ (SEQ ID NO: 4), linear peptide Gly-Leu-Asn-Gly-Glu-$NH_2$ (SEQ ID NO: 9), linear peptide Gly-Leu-Hyp-Gly-Glu-$NH_2$ (SEQ ID NO: 14).

Results showed that the treatment with $CCl_4$ significantly induced collagen production in the liver (marker of matrix accumulation), and the cyclic peptide Pro-Gly-Leu-Gln-Gly-Glu (SEQ ID NO: 6) was able to significantly reduce collagen accumulation. Also the linear peptide GLQGE-$NH_2$ (SEQ ID NO: 4) was able to significantly reduce $CCl_4$-induced collagen accumulation. In contrast neither the cyclic forms of the control peptides (with Pro: Pro-Gly-Leu-Asn-Gly-Glu (SEQ ID NO: 11) or Pro-Gly-Leu-Hyp-Gly-Glu (SEQ ID NO: 16) nor the linear forms of the control peptides Gly-Leu-Asn-Gly-Glu-$NH_2$ (SEQ ID NO: 9) and Gly-Leu-Hyp-Gly-Glu-$NH_2$ (SEQ ID NO: 14) were able to reduce collagen amount in the liver. Thus, the peptides of sequence Gly-Leu-Gln-Gly-Glu (SEQ ID NO: 2) in both linear and cyclic form are able to inhibit excess accumulation of extracellular matrix, and could be useful to prevent fibrosis progression (FIG. 1).

Example 3: Effect of cyclic peptides (without proline) and acetylated linear peptides on chemically induced liver fibrosis in mice.

Mice were injected for 6 weeks with $CCl_4$ in order to induce liver fibrosis. Starting on day 32 the mice received daily intraperitoneal injections of the peptides at a final dose of 25 mg/kg/mouse/day diluted in NaCl 0.9% for a total of 10 days. In these experiments, the following peptides were tested: cyclic peptide Gly-Leu-Gln-Gly-Glu (SEQ ID NO: 5), cyclic peptide Gly-Leu-Asn-Gly-Glu (SEQ ID NO: 10), cyclic peptide Gly-Leu-Hyp-Gly-Glu (SEQ ID NO: 15), linear peptide Ac-Gly-Leu-Gln-Gly-Glu (SEQ ID NO: 3), linear peptide Ac-Gly-Leu-Asn-Gly-Glu (SEQ ID NO: 8), linear peptide Ac-Gly-Leu-Hyp-Gly-Glu (SEQ ID NO: 13).

Results showed that the treatment with $CCl_4$ significantly induced collagen production in the liver (marker of matrix accumulation), and the cyclic peptide Gly-Leu-Gln-Gly-Glu (SEQ ID NO: 5) was able to significantly reduce collagen accumulation. Also the linear peptide Ac-Gly-Leu-Gln-Gly-Glu (SEQ ID NO: 3) was able to significantly reduce $CCl_4$-induced collagen accumulation. In contrast neither the cyclic forms nor the linear forms of the peptides Ac-Gly-Leu-Asn-Gly-Glu (SEQ ID NO: 8) and Ac-Gly-Leu-Hyp-Gly-Glu (SEQ ID NO: 13) were able to reduce collagen amount in the liver. Thus, the peptides of sequence Gly-Leu-Gln-Gly-Glu (SEQ ID NO: 2) in both linear and cyclic form are able to inhibit excess accumulation of extracellular matrix, and could be useful to prevent fibrosis progression.

Figure 2:
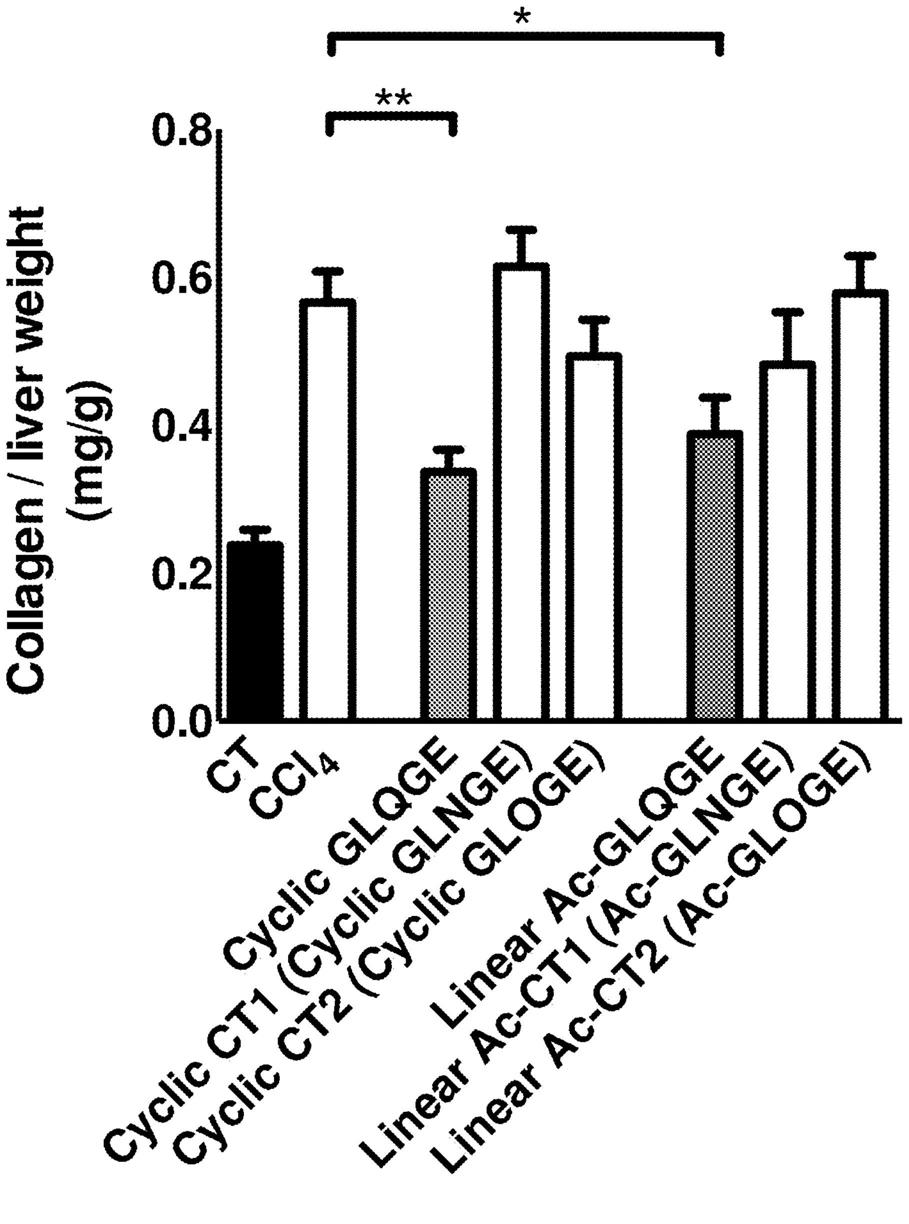
FIG. 2 Prevention of fibrosis progression by cyclic peptides and acetylated linear peptides. Mice were injected for 6 weeks with $CCl_4$ in order to induce liver fibrosis. Starting on day 32 the mice received daily intraperitoneal injections of 25 mg/kg/mouse/day of the peptides in 0.9% NaCl for a total of 10 days. $CCl_4$-treated mice also received NaCl 0.9%. The healthy control group (CT) only received 0.9% NaCl. N=5/18/9/9/6/5/4/4 in two experiments. The following peptides were tested on $CCl_4$-treated mice: cyclic Gly-Leu-Gln-Gly-Glu (Cyclic GLQGE; SEQ ID NO: 5), and compared to two controls: cyclic Gly-Leu-Asn-Gly-Glu (Cyclic CT1: cyclic GLNGE; SEQ ID NO: 10) and cyclic Gly-Leu-Hyp-Gly-Glu (Cyclic CT2: cyclic GLOGE; SEQ ID NO: 15). Linear Ac-Gly-Leu-Gln-Gly-Glu (Linear Ac-GLQGE; SEQ ID NO: 3) was also tested and compared to two controls: linear Ac-Gly-Leu-Asn-Gly-Glu (Linear Ac-CT1: linear Ac-GLNGE; SEQ ID NO: 8) and linear Ac-Gly-Leu-Hyp-Gly-Glu (Linear Ac-CT2: linear Ac-GLOGE; SEQ ID NO: 13). * $p<0.05$, ** $p<0.005$. Evaluated by t-test. Data presented as mean+SEM.

Moreover, the cyclic peptide Gly-Leu-Gln-Gly-Glu (SEQ ID NO: 5) was more efficient in reducing collagen accumulation also in comparison to the cyclic peptide with proline Pro-Gly-Leu-Gln-Gly-Glu (SEQ ID NO: 6) (compare the values on the Y-axis of FIGS. 1 and 2, the difference is statistically significant, $p<0.001$).

Example 4: Effect of hydrochloride salt of the cyclic peptide Gly-Leu-Gln-Gly-Glu (cyclic GLQGE) on cancer in mice.

Figure 3:
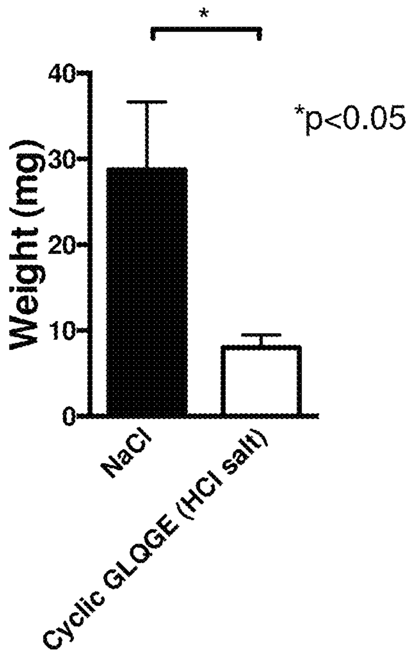
FIG. 3 Prevention of cancer growth by cyclic GLQGE (SEQ ID NO: 5) in form of hydrochloride salt (cyclic GLQGE HCl salt). B16 melanoma cancer cells were injected subcutaneously in mice. On day 7, injection with 1 mg of the peptide or 0.9% NaCl subcutaneously was performed. On day 12 mice were euthanized and tumors removed and weighed. N=11/11 mice. Data presented as mean+SEM.

The cyclic peptide Gly-Leu-Gln-Gly-Glu (cyclic GLQGE; SEQ ID NO: 5) in form of hydrochloride salt was tested for its ability in prevention of cancer growth in a melanoma model in mice. B16 melanoma cancer cells ($10^6$ cells) were injected subcutaneously in mice. On day 7, injection with 1 mg of the cyclic GLQGE peptide (SEQ ID NO: 5) or 0.9% NaCl (control mice) subcutaneously was performed. On day 12 mice were euthanized and tumours removed and weighed. N=11/11 mice. Results are shown on FIG. 3 as mean+SEM. Analysis of tumor weight in control and treated mice showed that the cyclic peptide Gly-Leu-Gln-Gly-Glu (SEQ ID NO: 5) (HCl salt) was significantly able to diminish cancer size of approximately 72% as compared to control mice. Thus, the cyclic peptide Gly-Leu-Gin-Gly-Glu (SEQ ID NO: 5) represents a promising therapeutic drug for use in the treatment of cancer.

Example 5: Effect of the cyclic peptide Gly-Leu-Gln-Gly-Glu (cyclic GLQGE) in form of acetate salt on chemically induced lung fibrosis in mice.

Figure 4:
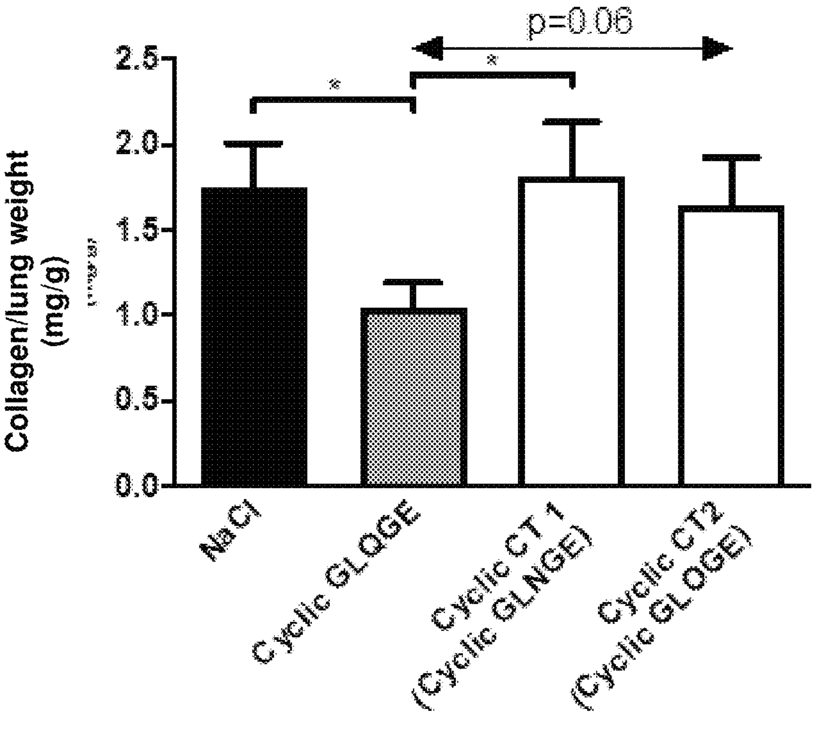
FIG. 4 Prevention of fibrosis progression by the cyclic peptide Gly-Leu-Gln-Gly-Glu (SEQ ID NO: 5) (acetate salt). Lung fibrosis was induced in 6-week-old male C57bl/6 mice using intratracheal bleomycin instillation at a dose of 0.005 units in 50 μl on day 0. Starting on day 11, cyclic Gly-Leu-Gln-Gly-Glu (cyclic GLQGE; SEQ ID NO: 5) was injected subcutaneously at a dose of 1 mg/mouse/day in 0.9% NaCl for a total of 10 days. The control group only received daily injections of 0.9% NaCl. The number of animals in the four groups was N=14/10/10/9 in three experiments. The cyclic peptide Gly-Leu-Gln-Gly-Glu (Cyclic GLQGE; SEQ ID NO: 5) (acetate salt) was tested and compared to cyclic Ac-Gly-Leu-Asn-Gly-Glu (Cyclic GLNGE; SEQ ID NO: 10) (acetate salt) and to cyclic Ac-Gly-Leu-Hyp-Gly-Glu (Cyclic GLOGE; SEQ ID NO: 15) (acetate salt), *$p<0.05$. Evaluated by t-test. Data are presented as mean ±SEM.

The cyclic peptide Gly-Leu-Gln-Gly-Glu (cyclic GLQGE (SEQ ID NO: 5) acetate salt) was tested for its ability in prevention of lung fibrosis in mice. Lung fibrosis was induced in 6-week-old male C57bl/6 mice using intratracheal bleomycin instillation at a dose of 0.005 units in 50 µl 0.9% NaCl on day 0. Starting on day 11, cyclic Gly-Leu-Gln-Gly-Glu (cyclic GLQGE; SEQ ID NO: 5) or the control cyclic Gly-Leu-Asn-Gly-Glu (Cyclic GLNGE; SEQ ID NO: 10) or the control cyclic Gly-Leu-Hyp-Gly-Glu (Cyclic GLOGE; SEQ ID NO: 15) (all three in form of acetate salt) was injected subcutaneously at a dose of 1 mg/mouse/day for 10 days. Results showed that administration of cyclic Gly-Leu-Gln-Gly-Glu (SEQ ID NO: 5) (acetate salt) significantly diminished the total amount of collagen in the lung compared to mice that received bleomycin alone ($p<0.05$) or with the control peptides cyclic Gly-Leu-Asn-Gly-Glu (SEQ ID NO: 10) (Cylic GLNGE acetate salt) or cyclic Gly-Leu-Hyp-Gly-Glu (SEQ ID NO: 15) (Cyclic GLOGE acetate salt) (FIG. 4).

Example 6: Effect of the cyclic peptide Gly-Leu-Gln-Gly-Glu (HCl salt) on breast cancer model in mice.

Figure 5:
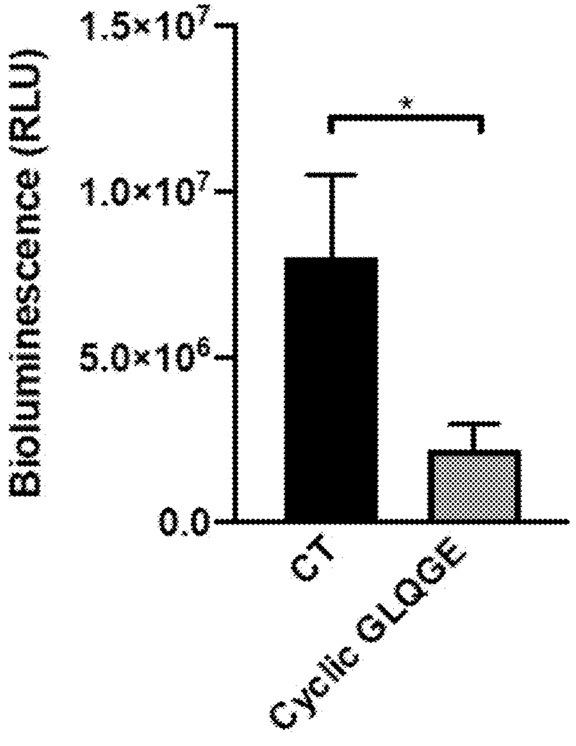
FIG. 5 Prevention of breast cancer growth by cyclic GLQGE (SEQ ID NO: 5) in form of hydrochloride salt (cyclic GLQGE HCl salt). Cells from the breast cancer cell line MDA-MB-231 were injected intratibially in mice. Starting on day 30, injection with 0.1 mg/mouse/day of the cyclic peptide Gly-Leu-Gln-Gly-Glu (SEQ ID NO: 5) (cyclic GLQGE HCl salt) for 10 days or 0.9% NaCl subcutaneously was performed. On day 40, the size of the tumour was evaluated by bioluminescence imaging (Bioluminescence imaging was performed by detecting photon signal 5 minutes after D-luciferin injection (150 mg/kg) using an "IVIS Lumina II" imaging system. The resulting images were analysed using the software "Living Image"). RLU=relative light units. The number of animals in each group was N=14/7 mice, in two experiments. * $p<0.05$ as evaluated by t-test. Data are presented as mean+SEM.

The hydrochloride salt of cyclic peptide Gly-Leu-Gln-Gly-Glu (cyclic GLQGE; SEQ ID NO: 5) was tested for its ability in prevention of breast cancer in mice. A bone lesion of metastatic breast cancer was induced by injecting cells from the breast cancer cell line MDA-MB-231 intratibially in CD1 nude mice. Starting on day 30, injection with 0.1 mg of the cyclic peptide Gly-Leu-Gin-Gly-Glu (SEQ ID NO: 5) (Cyclic GLQGE HCl salt) or 0.9% NaCl subcutaneously was performed daily for 10 days. On day 40, the size of the tumor was evaluated by bioluminescence imaging (Bioluminescence imaging was performed by detecting photon signal 5 minutes after D-luciferin injection (150 mg/kg) using an "IVIS Lumina II" imaging system. The resulting images were analyzed using the software "Living Image"). The number of animals in the control and treated group was N=14/7 mice in two experiments. Results showed that administration of cyclic Gly-Leu-Gln-Gly-Glu (SEQ ID NO: 5) (HCl salt) significantly ($p<0.05$) diminished the size of the tumor compared to mice that received 0.9% NaCl (FIG. 5).

What is claimed is:

1. A peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and a pharmaceutically acceptable salt thereof.

2. The peptide according to claim 1, wherein Xa is selected from Gly and Ac-Gly and Xb is selected from Glu and Glu-$NH_2$, and the pharmaceutically acceptable salt thereof.

3. The peptide according to claim 1, wherein Xa is Ac-Gly and Xb is Glu (SEQ ID NO: 3) or Xa is Gly and Xb is Glu-$NH_2$ (SEQ ID NO: 4).

4. The peptide according to claim 1, wherein Xa is Gly and Xb is Glu and Glu binds to Gly to form the cyclic peptide (SEQ ID NO: 5):

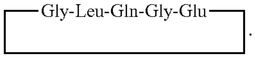.

5. The peptide according to claim 1, wherein Xa is Pro-Gly and Xb is Glu and Pro binds to Glu to form the cyclic peptide (SEQ ID NO: 6):

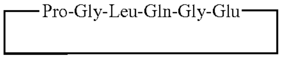.

6. A pharmaceutical composition comprising the peptide Xa-Leu-Gln-Gly-Xb (SEQ ID NO: 1) according to claim 1, together with at least one pharmaceutically acceptable vehicle, excipient and/or diluent.

7. The pharmaceutical composition according to claim 6, wherein Xa is selected from Gly and Ac-Gly and Xb is selected from Glu and Glu-$NH_2$, and the pharmaceutically acceptable salt thereof.

8. The pharmaceutical composition according to claim 6, wherein Xa is Ac-Gly and Xb is Glu (SEQ ID NO: 3) or Xa is Gly and Xb is Glu-$NH_2$ (SEQ ID NO: 4).

9. The pharmaceutical composition according to claim 6, wherein the peptide is (SEQ ID NO: 5)

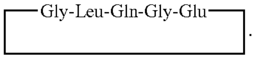.

10. The pharmaceutical composition according to claim 6, wherein the peptide is (SEQ ID NO: 6)

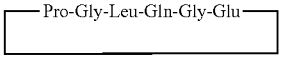.

11. A method for the treatment of a fibrotic condition characterized by an excess accumulation of extracellular matrix in a tissue or an organ, comprising administering to a patient a therapeutically effective amount of a peptide consisting of the general sequence Xa-Leu-Gln-Gly-Xb (SEQ ID NO: 1), wherein Xa is selected from Pro-Gly, Gly and Ac-Gly and Xb is selected from Glu and Glu-$NH_2$, and/or a pharmaceutically acceptable salt thereof, wherein the accumulation of extracellular matrix in said tissue or organ is reduced from the level existing at the time of treatment.

12. The method according to claim 11, wherein the fibrotic condition is selected from the group consisting of liver fibrosis, cirrhosis of the liver, lung fibrosis, chronic respiratory failure, cardiac fibrosis, ischemic heart disease, heart failure, diabetic nephropathy, glomerulonephritis, myelofibrosis, breast cancer, uterus cancer, prostate cancer, pancreas cancer, colon cancer, skin cancer, blood cell cancers, cancers of the central nervous system, fibroids, fibroma, fibroadenomas and fibrosarcomas.

13. The method according to claim 11, wherein the peptide is Xa-Leu-Gln-Gly-Xb (SEQ ID NO: 1), wherein Xa is Ac-Gly and Xb is Glu (SEQ ID NO: 3) or Xa is Gly and Xb is Glu-$NH_2$ (SEQ ID NO: 4).

14. The method according to claim 11, wherein the peptide is (SEQ ID NO: 5)

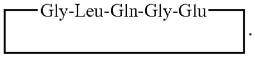.

15. The method according to claim 11, wherein the peptide is (SEQ ID NO: 6)

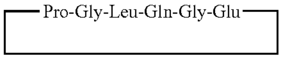.

16. The method according to claim 12, wherein the peptide is Xa-Leu-Gln-Gly-Xb (SEQ ID NO: 1), wherein Xa is Ac-Gly and Xb is Glu (SEQ ID NO: 3) or Xa is Gly and Xb is Glu-$NH_2$ (SEQ ID NO: 4).

17. The method according to claim 12, wherein the peptide is (SEQ ID NO: 5)

Gly-Leu-Gln-Gly-Glu.

18. The method according to claim 12, wherein the peptide is (SEQ ID NO: 6)

Pro-Gly-Leu-Gln-Gly-Glu.

* * * * *